United States Patent [19]
Karin et al.

[11] Patent Number: 5,837,244
[45] Date of Patent: Nov. 17, 1998

[54] ONCOPROTEIN PROTEIN KINASE

[75] Inventors: Michael Karin; Masahiko Hibi, both of San Diego; Anning Lin, La Jolla, all of Calif.

[73] Assignee: The Regents of the University of California, Oakland, Calif.

[21] Appl. No.: 711,893

[22] Filed: Sep. 12, 1996

Related U.S. Application Data

[60] Division of Ser. No. 276,860, Jul. 18, 1994, Pat. No. 5,593,884, which is a continuation-in-part of Ser. No. 220,602, Mar. 25, 1994, which is a continuation-in-part of Ser. No. 94,533, Jul. 19, 1993, Pat. No. 5,534,426.

[51] Int. Cl.[6] .......................... A61K 31/90; A61K 39/395
[52] U.S. Cl. ......................... 424/139.1; 435/194; 514/44
[58] Field of Search ........................... 424/139.1; 514/44; 435/194

[56] References Cited

PUBLICATIONS

Derijard, B., et al. (1994) Cell 76, 1–20.
Cano, E., et al. (1995) TIBS 20, 117–112.
Hibi, M., et al. (1993) Genes and Development 7, 2135–2148.
Minden, A., et al. (1994) Mol. Cell. Biol. 14 (10), 6683–6688.
Pulverer, B.J. et al., (1991) Nature 353, 670–674.
Boulton, T.G., et al., (1991) Cell 65, 663–675.
Anderson, N.G., et al., (1990) Nature 343, 651–653.
Kyriakis, J.M., et al., (1990) J. Biol Chem 265(28), 17355–17363.
Adler, V. et al. (1992) Proc. Natl. Acad. Sci, USA, 89, 5341–5345.
Segel, I.H. (1976) Biochemical Calculations, John Wiley & Sons, Inc. N.Y., p. 246.
Boulton, et al. (1990) Science 249, 64–67.

*Primary Examiner*—Charles L. Patterson, Jr.
*Attorney, Agent, or Firm*—Fish & Richardson, P.C.

[57] ABSTRACT

An isolated polypeptide (JNK) characterized by having a molecular weight of 46 kD as determined by reducing SDS-PAGE, having serine and threonine kinase activity, phosphorylating the c-Jun N-terminal activation domain and polynucleotide sequences and method of detection of JNK are provided herein. JNK phosphorylates c-Jun N-terminal activation domain which affects gene expression from AP-1 sites.

3 Claims, 26 Drawing Sheets

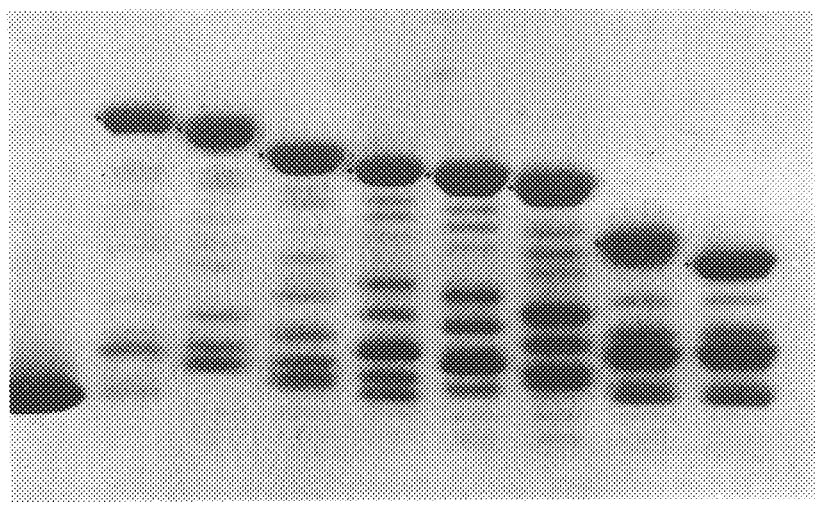
FIG. 6A Protein Gel
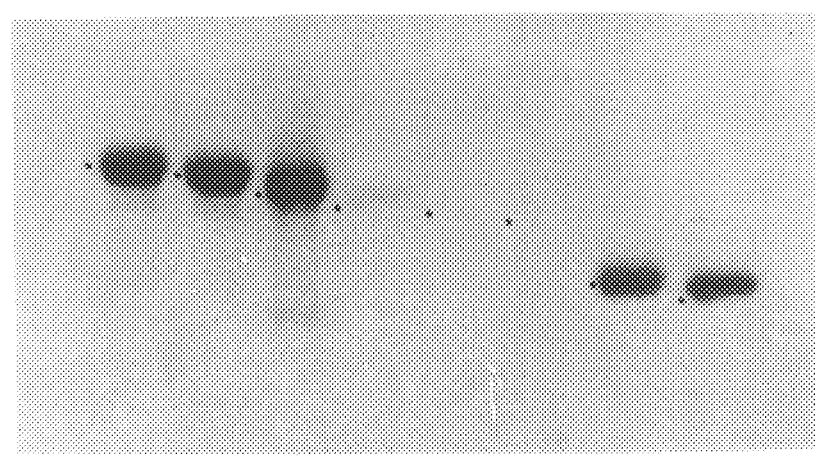
FIG. 6B ³²P-Immobilized Substrate
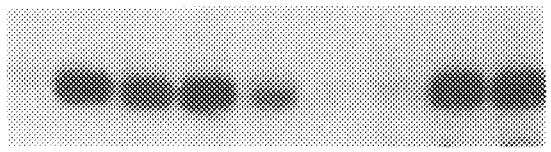
FIG. 6C ³²P-Exogenous Substrate

GAATTCCGGG GCGGCCAAGA CCCGCCGCCG GCCGGCCACT GCAGGGTCCG CACTGATCCG  60

CTCCGGGGGA GAGCCCGCTG TCTGGGAAGT CAGTTCGCCT GCCGGACTCCG AGGAACCGCT 120

GCGCACGAAG AGCCGTCAGT GAGTGACCGC GACTTTTCAA AGCCGGGTAG GGCGGGCGAG 180

TCGACAAGTA AGAGTGCGGG AGGCATCTTA ATTAACCCTG CGCTCCCCTGG AGCAGCTGGT 240

GAGGAGGGCG CACGGGGACG ACAGCCAGCC GGTGCGTGCG CTCTTAGAGA AACTTTCCCT 300

GTCAAAGGCT CCGGGGGGCC CGGGTGTCCC CCGCTTGCCA CAGCCCTGTT GCGGCCCCGA 360

AACTTGTGCG CGCACGCCAA ACTAACCTCA CGTGAAGTGA CGGACTGTTC 417
                                                     Met Thr
                                                      1

GCA AAG ATG GAA ACG ACC TTC TAT GAC GAT GCC CTC AAC GCC TCG TTC 465
Ala Lys Met Glu Thr Thr Phe Tyr Asp Asp Ala Leu Asn Ala Ser Phe
          5                  10                  15

CTC CCC TCC GAG AGG GGA CCT TAT GGC TAC AGT AAC CCC AAG ATC CTG 513
Leu Pro Ser Glu Arg Gly Pro Tyr Gly Tyr Ser Asn Pro Lys Ile Leu
 20                  25                  30

AAA CAG AGC ATG ACC CTG AAC CTG GCC GAC CCA GTG GGG AGC CTG AAG 561
Lys Gln Ser Met Thr Leu Asn Leu Ala Asp Pro Val Gly Ser Leu Lys
 35                  40                  45                  50

```
CCG CAC CTC CGC GCC AAG AAC TCG GAC CTC CTC ACC TCG CCC GAC GTG    609
Pro His Leu Arg Ala Lys Asn Ser Asp Leu Leu Thr Ser Pro Asp Val
                55              60              65

GGG CTG CTC AAG CTG GCG TCG CCC GAG CGC CTG ATA ATC CAG             657
Gly Leu Leu Lys Leu Ala Ser Pro Glu Arg Leu Ile Ile Gln
            70              75              80

TCC AGC AAC GGG CAC ATC ACC CCC GAG CAG ACC CCC ACC CTG TTC CTG    705
Ser Ser Asn Gly His Ile Thr Pro Glu Gln Thr Pro Thr Leu Phe Leu
            85              90              95

TGC CCC AAG GTG AAC GTG ACA GAT GAG CAG GAG CAG GGG TTC GCC GGC TTC CTG   753
Cys Pro Lys Val Asn Val Thr Asp Glu Gln Glu Gln Gly Phe Ala Gly Phe Leu
        100             105             110

GTG CGC GCC CTG GCC GAA CTG CAC AGC CAG AAC ACG CTG CCC AGC GTC    801
Val Arg Ala Leu Ala Glu Leu His Ser Gln Asn Thr Leu Pro Ser Val
        115             120             125             130

ACG TCG GCG GCA CAG CCG GTC AAC GGG GCA GCA ATG GTG GCT CCC GCG    849
Thr Ser Ala Ala Gln Pro Val Asn Gly Ala Ala Met Val Ala Pro Ala
        135             140             145

GTA GCC TCG GTG GCA GGG GGC AGC AGC GGG GGC TTC AGC GCC AGC        897
Val Ala Ser Val Ala Gly Gly Ser Ser Gly Gly Phe Ser Ala Ser
        150             155             160
```

| | | | | | | | | | | | | | | | | |
|---|---|---|---|---|---|---|---|---|---|---|---|---|---|---|---|---|
| CTG<br>Leu | CAC<br>His<br>165 | AGC<br>Ser | GAG<br>Glu | CCG<br>Pro | CCG<br>Pro | GTC<br>Val | TAC<br>Tyr<br>170 | GCA<br>Ala | AAC<br>Asn | CTC<br>Leu | AGC<br>Ser | AAC<br>Asn<br>175 | TTC<br>Phe | AAC<br>Asn | CCA<br>Pro | 945 |
| GGC<br>Gly | GCG<br>Ala<br>180 | CTG<br>Leu | AGC<br>Ser | GGC<br>Gly | AGC<br>Ser | GGC<br>Gly<br>185 | GGC<br>Gly | GCG<br>Ala | CCC<br>Pro | TCC<br>Ser | TAC<br>Tyr<br>190 | GGC<br>Gly | GCC<br>Ala | GGC<br>Gly | | 993 |
| CTG<br>Leu | GCC<br>Ala<br>195 | TTT<br>Phe | CCC<br>Pro | GCG<br>Ala | CAA<br>Gln | CCC<br>Pro<br>200 | CAG<br>Gln | CAG<br>Gln | CAG<br>Gln | CAG<br>Gln | CCG<br>Pro<br>205 | CAC<br>His | CAC<br>His<br>210 | | | 1041 |
| CTG<br>Leu | CCC<br>Pro | CAG<br>Gln | CAG<br>Gln<br>215 | ATG<br>Met | GTG<br>Val | CCC<br>Pro | GTG<br>Val | CAG<br>Gln | CAC<br>His<br>220 | CCG<br>Pro | CGG<br>Arg | CTG<br>Leu | CAG<br>Gln | GCC<br>Ala<br>225 | CTG<br>Leu | AAG<br>Lys |
| | | | | | | | | | | | | | | | | 1089 |
| GAG<br>Glu | GAG<br>Glu<br>230 | CCT<br>Pro | CAG<br>Gln | ATA<br>Ile | GTG<br>Val | CCC<br>Pro<br>235 | GAG<br>Glu | ATG<br>Met | CCC<br>Pro | GGC<br>Gly | GAG<br>Glu<br>240 | ACA<br>Thr | CCG<br>Pro | CCC<br>Pro | CTG<br>Leu | 1137 |
| TCC<br>Ser | CCC<br>Pro<br>245 | ATC<br>Ile | GAC<br>Asp | ATG<br>Met | GAG<br>Glu | TCC<br>Ser<br>250 | CAG<br>Gln | CGC<br>Arg | ATC<br>Ile | AAG<br>Lys | GCG<br>Ala<br>255 | GAG<br>Glu | AGG<br>Arg | AAG<br>Lys | | 1185 |
| CGC<br>Arg | ATG<br>Met<br>260 | AGG<br>Arg | AAC<br>Asn | CGC<br>Arg | ATC<br>Ile | GCT<br>Ala<br>265 | GCC<br>Ala | TCG<br>Ser | AAG<br>Lys | TGC<br>Cys | CGA<br>Arg<br>270 | AAA<br>Lys | AGG<br>Arg | AAG<br>Lys | CTG<br>Leu | 1233 |

FIG. 10C

```
GAG AGA ATC GCC CGG CTG GAG GAA AAA GTG AAA ACC TTG AAA GCT CAG      1281
Glu Arg Ile Ala Arg Leu Glu Glu Lys Val Lys Thr Leu Lys Ala Gln
275                 280                 285                 290

AAC TCG GAG CTG GCG TCG ACG GCC AAC ATG CTC AGG GAA CAG GTC GCA      1329
Asn Ser Glu Leu Ala Ser Thr Ala Asn Met Leu Arg Glu Gln Val Ala
            295                 300                 305

CAG CTT AAA CAC AAA GTC ATG AAC CAC GTT AAC AGT GGG TGC CAA CTC      1377
Gln Leu Lys His Lys Val Met Asn His Val Asn Ser Gly Cys Gln Leu
        310                 315                 320

ATC CTA ACG CAG CAG TTG CAA ACA TTT TGAAGAGAGA CCGTCGGGGG            1424
Ile Leu Thr Gln Gln Leu Gln Thr Phe
    325                 330

CTGAGGGGCA ACGAAGAACA AAAATAACAC AGAGAGAAAA ACTTGAGAAC TTGACAAGTT    1484

GCGACGGAGA GAAAAAAGAA GTGTCCGAGA ACTAAAGCCA AGGGTATCCA AGTTGGACTG    1544

GGTTCGGTCT GACGGCGCCC CCAGTGTGCA CGAGTGGGAA CCACCTGGTC GCGCCCTCCC    1604

TTGGCTCGA GCCAGGGAGC GGCCGCCTGG GGGCCTGCCC GCTTTGCGGA CGGGCTGTCC    1664

CCGGCGAAC GGAACGTTGG ACTTTCGTTA ACATTGACCA AGAACTGCAT GGACCTAACA    1724
```

FIG. IOD

```
TTCGATCTCA TTCAGTATTA AAGGGGGCAG GGGGAGGGGG TTACAAACTG CAATAGAGAC  1784
TGTAGATTGC TTCTGTAGTA CTCCTTAAGA ACACAAAGCG GGGGAGGGT  TGGGGAGGGG  1844
CGGCAGGAGG GAGGTTTGTG AGAGCGAGGC TGAGCCTACA GATGAACTCT TTCTGGCCTG  1904
CTTCGGTTAA CTGTGTATGT ACATATATAT ATTTTTAAT  TTGATTAAAG CTGATTACTG  1964
TCAATAAACA GCTTCATGCC TTTGTAAGTT ATTTCTTGTT TGTTTGTTTG GGATCCTGCC  2024
CAGTGTTGTT TGTAAATAAG AGATTGGAG  CACTCTGAGT TTACCATTTG TAATAAAGTA  2084
TATAATTTTT TT                                                      2096
```

FIG. 10E

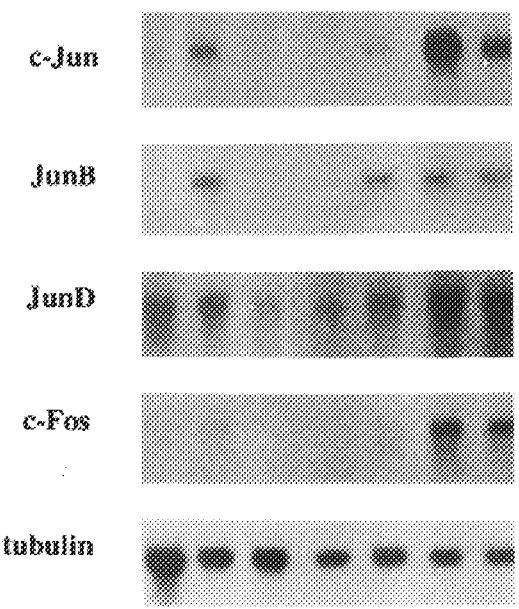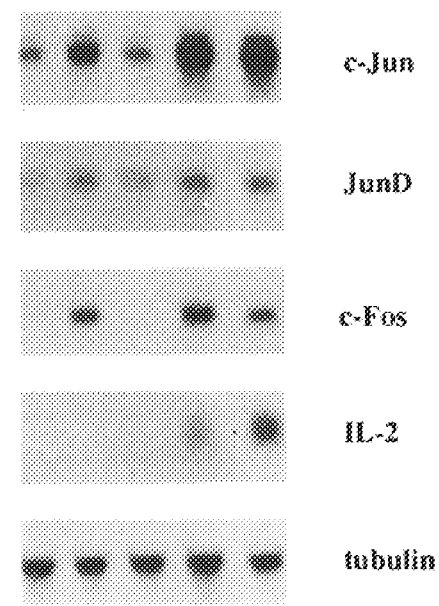
FIG. IIA   FIG. IIB

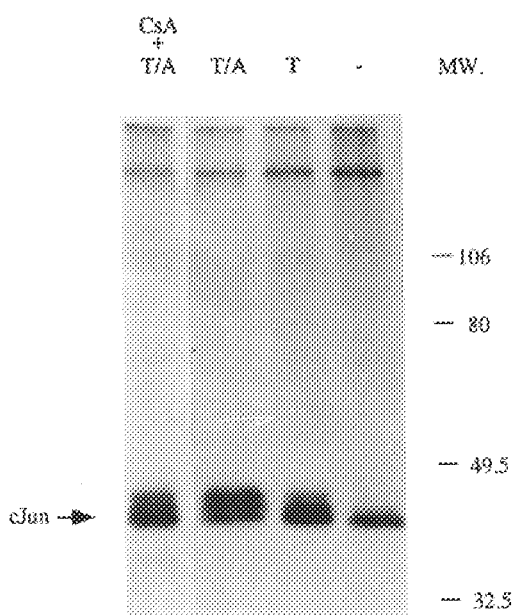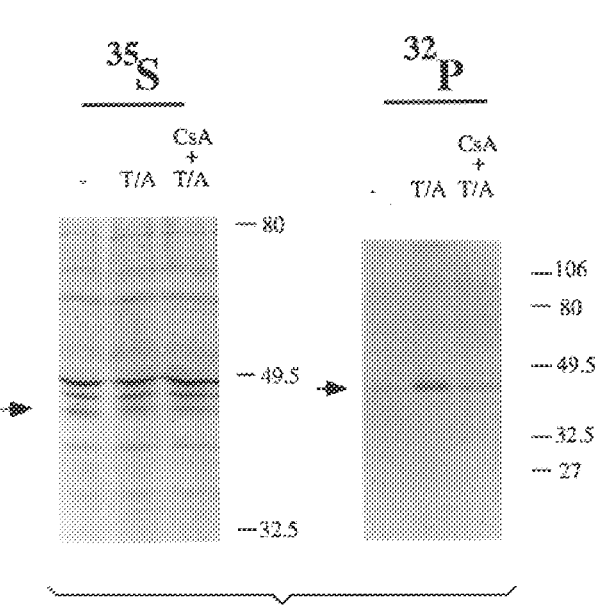

Erk-1 Mut →

Erk-1 Mut →

MBP →

MBP →

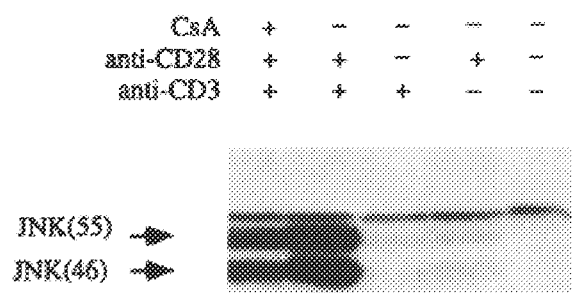
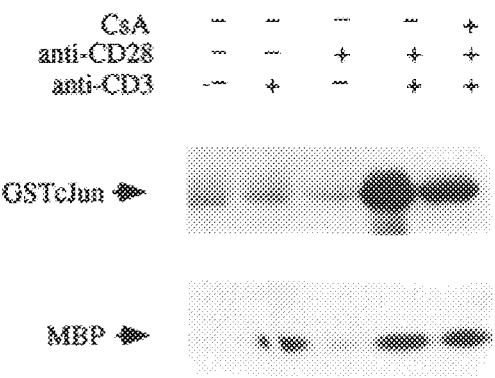
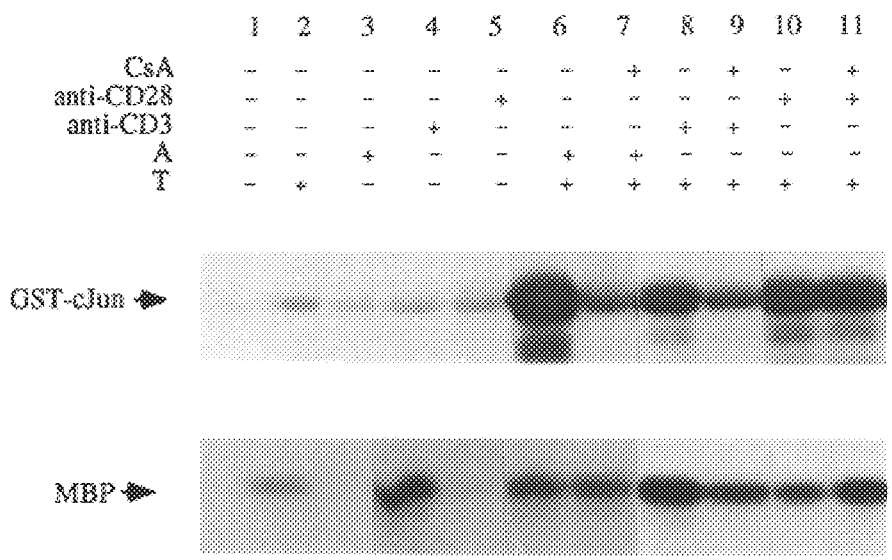

ONCOPROTEIN PROTEIN KINASE

This is a divisional of application Ser. No. 08/276,860 filed Jul. 18, 1994 now U.S. Pat. No. 5,593,884, which is a continuation-in-part application of U.S. Ser. No. 08/220,602, filed Mar. 25, 1994, which is a continuation-in-part application of U.S. Ser. No. 08/094,533 filed Jul. 19, 1993 now U.S. Pat. No. 5,534,426.

BACKGROUND OF THE INVENTION

This invention was made with support by Howard Hughes Medical Institute and Government support under Grant No. DE-86ER60429, awarded by the Department of Energy and Grant No. CA-50528 and CA-58396, awarded by the National Institute of Health. The Government has certain rights in this invention. Also supported by the Howard Hughes Medical Institute.

1. Field of the Invention

This invention relates generally to the field of protein kinases, oncogenes and oncoproteins and, specifically, to a protein kinase which binds, phosphorylates and potentiates the c-Jun N-terminal activation domain.

2. Description of Related Art

A number of viral and cellular genes have been identified as potential cancer genes, collectively referred to as oncogenes. The cellular homologs of viral oncogenes, the proto-oncogenes or c-oncogenes, act in the control of cell growth and differentiation or mediate intracellular signaling systems. The products of oncogenes are classified according to their cellular location, for example, secreted, surface, cytoplasmic, and nuclear oncoproteins.

Proto-oncogenes which express proteins which are targeted to the cell nucleus make up a small fraction of oncogenes. These nuclear proto-oncoproteins typically act directly as transactivators and regulators of RNA and DNA synthesis. Nuclear oncogene products have the ability to induce alterations in gene regulation leading to abnormal cell growth and ultimately neoplasia. Examples of nuclear oncogenes include the myc, ski, myb, fos and jun genes.

The c-Jun protein, encoded by the c-jun proto-oncogene, is an important component of the dimeric, sequence specific, transcriptional activator, AP-1. Like other transcriptional activators, c-Jun contains two functional domains, including a DNA binding domain and a transactivation domain. The DNA binding domain is located at the C-terminus and is a BZip structure which consists of conserved basic (B) and leucine zipper (Zip) domains that are required for DNA binding and dimerization, respectively. The N-terminus contains the transactivation domain. Although c-Jun expression is rapidly induced by many extracellular signals, its activity is also regulated post-translationally by protein phosphorylation. Phosphorylation of sites clustered next to c-Jun's DNA binding domain inhibits DNA binding (Boyle, et al., Cell, 64:573, 1991; Lin, et al., Cell, 70:777, 1992). Phosphorylation of two other sites, Ser 63 and Ser 73, located within the transactivation domain, potentiates c-Jun's ability to activate transcription (Binetruy, et al., Nature 351:122, 1991; Smeal, et al., Nature 354:494, 1991). Phosphorylation rates of these sites are low in non-stimulated cells and are rapidly increased in response to growth factors such as platelet derived growth factor (PDGF) or v-Sis, or expression of oncogenically activated Src, Ras and Raf proteins. In myeloid and lymphoid cells, phosphorylation of these sites is stimulated by the phorbol ester, TPA, but not in fibroblasts and epithelial cells. These differences may be due to different modes of Ha-ras regulation in lymphoid cells versus fibroblasts.

Many proteins cooperate with each other in the activation of transcription from specific promoters. Through this cooperation, a gene can be transcribed and a protein product generated. Members of the Fos proto-oncogene family, along with members of the Jun gene family, form stable complexes which bind to DNA at an AP-1 site. The AP-1 site is located in the promoter region of a large number of genes. Binding of the Fos/Jun complex activates transcription of a gene associated with an AP-1 site. In cells that have lost their growth regulatory mechanisms, it is believed that this Fos/Jun complex may "sit" on the AP-1 site, causing overexpression of a particular gene. Since many proliferative disorders result from the overexpression of an otherwise normal gene, such as a proto-oncogene, it would be desirable to identify compositions which interfere with the excessive activation of these genes.

For many years, various drugs have been tested for their ability to alter the expression of genes or the translation of their messages into protein products. One problem with existing drug therapy is that it tends to act indiscriminately and affects healthy cells as well as neoplastic cells. This is a major problem with many forms of chemotherapy where there are severe side effects primarily due to the action of toxic drugs on healthy cells.

In view of the foregoing, there is a need to identify specific targets in the abnormal cell which are associated with the overexpression of genes whose expression products are implicated in cell proliferative disorders, in order to decrease potential negative effects on healthy cells. The present invention provides such a target.

SUMMARY OF THE INVENTION

The present invention provides a novel protein kinase (JNK) which phosphorylates the c-Jun N-terminal activation domain. JNK1 is characterized by having a molecular weight of 46 kD (as determined by reducing SDS-polyacrylamide gel electrophoresis (PAGE)) and having serine and threonine kinase activity. Specifically, JNK1 phosphorylates serine residues 63 and 73 of c-Jun.

Since the product of the jun proto-oncogene is a transactivator protein which binds at AP-1 sites, regulation of c-Jun activation may be important in affecting normal gene expression and growth control in a cell. The discovery of JNK provides a means for identifying compositions which affect JNK activity, thereby affecting c-Jun activation and subsequent activation of genes associated with AP-1 sites.

The identification of JNK now allows the detection of the level of specific kinase activity associated with activation of c-Jun and AP-1. In addition, the invention provides a method of treating a cell proliferative disorder associated with JNK by administering to a subject with the disorder, a therapeutically effective amount of a reagent which modulates JNK activity.

The invention also provides a synthetic peptide comprising the JNK binding region on c-Jun which corresponds to amino acids 33–79. The peptide is useful as a competitive inhibitor of the naturally occurring c-Jun in situations where it is desirable to decrease the amount of c-Jun activation by JNK.

The invention also describes JNK2, a novel protein kinase with activity similar to JNK1 and having a molecular weight of 55 kD.

cells after incubation with $^{32}$P-ATP and GST-cJun (wt), GSTcJun(Ala63/73) or GST.

FIG. 2 shows an SDS-PAGE of A) HeLaS3 cells either untreated or irradiated with UV light and B) Jurkat cells either untreated or incubated with TPA. Cell extracts were incubated with $^{32}$P-ATP and GST-cJun (wt), GSTcJun-(Ala63/73) or GST.

FIG. 3 shows phosphopeptide mapping of GST-cJun and c-Jun phosphorylated by JNK. 3(A) shows maps of GSTcJun and (B) shows maps of c-Jun.

Figure 4A:
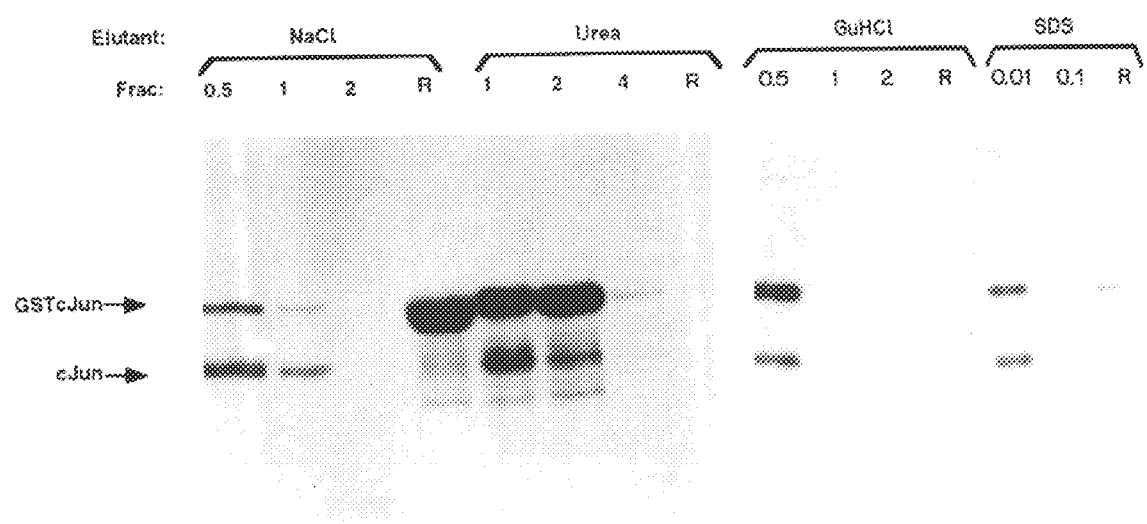
Figure 4B:
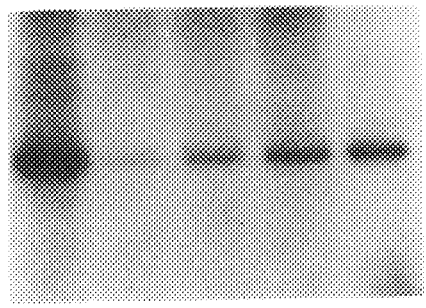

FIG. 4A shows an SDS-PAGE of phosphorylated proteins after elution of JNK from GSTc-Jun after washes of NaCl, Urea, Guanidine-HCl(GuHCl) or SDS. FIG. 4B shows an SDS-PAGE of phosphorylated c-Jun after GSTcJun(wt) was covalently linked to GSH-beads and incubated with whole cell extract of TPA-stimulated Jurkat cells.

FIG. 5 shows an in-gel kinase assay. GSTcJun-GSH agarose beads were incubated with cell extracts from A) TPA-stimulated Jurkat cells on SDS gels that were polymerized in the absence (−) or presence (+) of GSTcJun (wt); B) extracts of unstimulated or UV stimulated HeLa cells and unstimulated or TPA-stimulated Jurkat cells; and C) extracts from cells of logarithmically growing K562 and Ha-ras-transformed FR3T3, TPA-stimulated Jurkat and U937 cells and UV-irradiated HeLa, F9 and QT6 cells.

FIG. 6A is a protein gel of various GST c-Jun fusion proteins; FIG. 6B shows an SDS-PAGE of whole cell extracts of UV-irradiated Hela S3 cells after passage over GSH-beads containing the GST fusion proteins as shown in FIG. 6A; FIG. 6C shows an SDS-PAGE of phosphorylated GSTcJun fusion proteins eluted with 1 MNaCl from GSH-agarose beads.

Figure 7A:
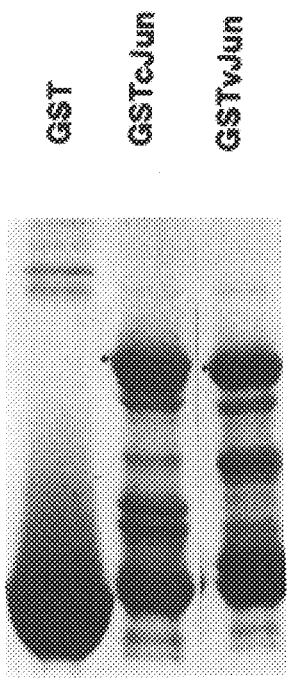
Figure 7B:
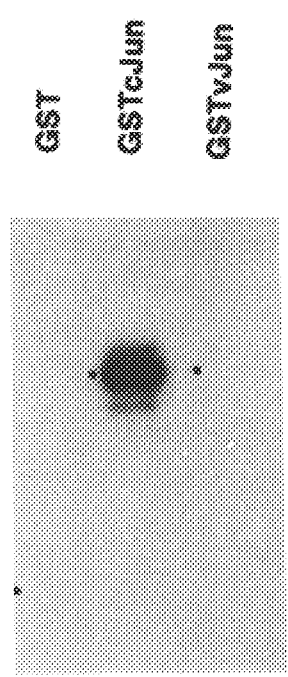
Figure 7C:
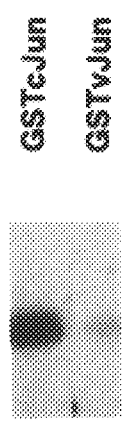

FIG. 7A shows patterns of GST, GSTcJun and GSTvJun as expressed in E. coli; FIG. 7B shows the phosphorylated proteins of 7A from extracts of TPA-activated Jurkat cells incubated with GSH-beads; FIG. 7C shows cJun protein after phosphorylation with protein bound to GSTcJun and GSTvJun beads.

FIG. 8 shows CAT activity in cells containing various portions of the c-Jun activation domain (cJ=AA1-223; 33=AA33-223; 43=AA43-223; 56=AA56-223; A63,73= AA1-246(Ala63/73)) and a CAT reporter in the absence or presence of A) Ha-ras or B) UV treatment.

Figure 9A:
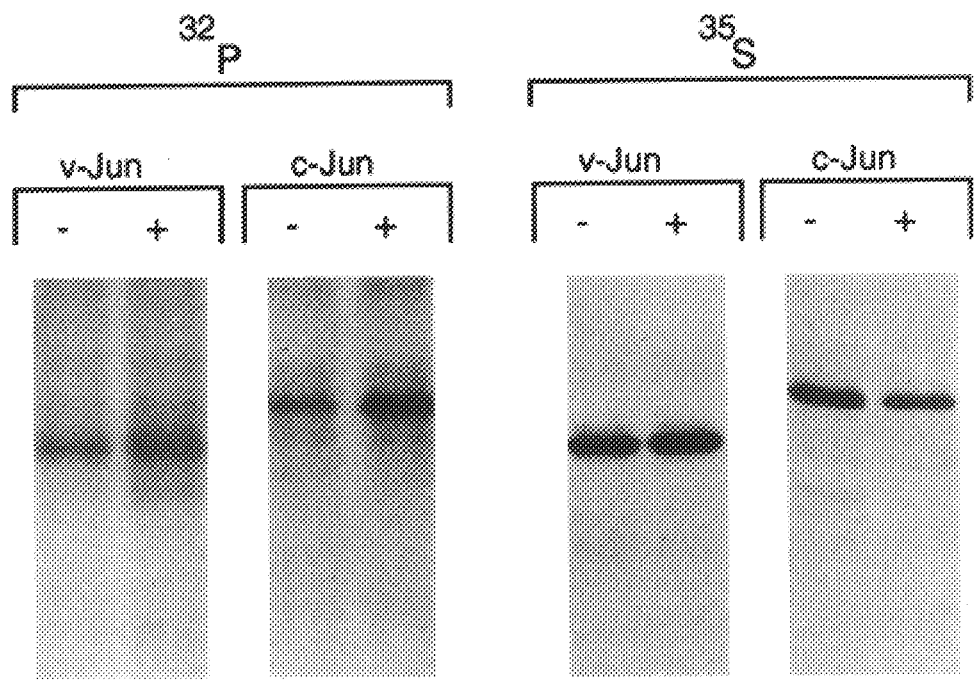

FIG. 9 shows SDS-PAGE analyses of $^{32}$P and $^{35}$S labelled F9 cells transfected with v-Jun and c-Jun in the absence or presence of A) Ha-ras or B) UV exposure.

FIG. 10 shows the nucleotide and deduced amino acid sequence of c-Jun. The arrows represent amino acid residues 33–79.

FIG. 11A shows a Northern blot of total cytoplasmic RNA from Jurkat cells. Cells were incubated with 50 ng/ml TPA (T), 1 μg/ml A23187 (A) or 100 ng/ml cyclosporin A (CsA) for 40 minutes, either alone or in combination, as indicated. Levels of c-jun, jun-B, jun-D, c-fos and α-tubulin expression were determined by hybridization to random primed cDNA probes.

FIG. 11B shows Jurkat cells after incubatation with soluble anti-CD3 (OKT3), 2 μg/ml soluble anti-CD28 (9.3) or a combination of 50 ng/ml TPA and 1 μg/ml A23817 (T/A) as indicated for 40 minutes. Total cytoplasmic RNA was isolated and 10 μg samples were analyzed using c-jun, jun-D and c-fos probes. IL-2 induction by the same treatments was measured after 6 hours of stimulation by blot hybridization using IL-2 and α-tubulin specific probes.

Figure 11C:
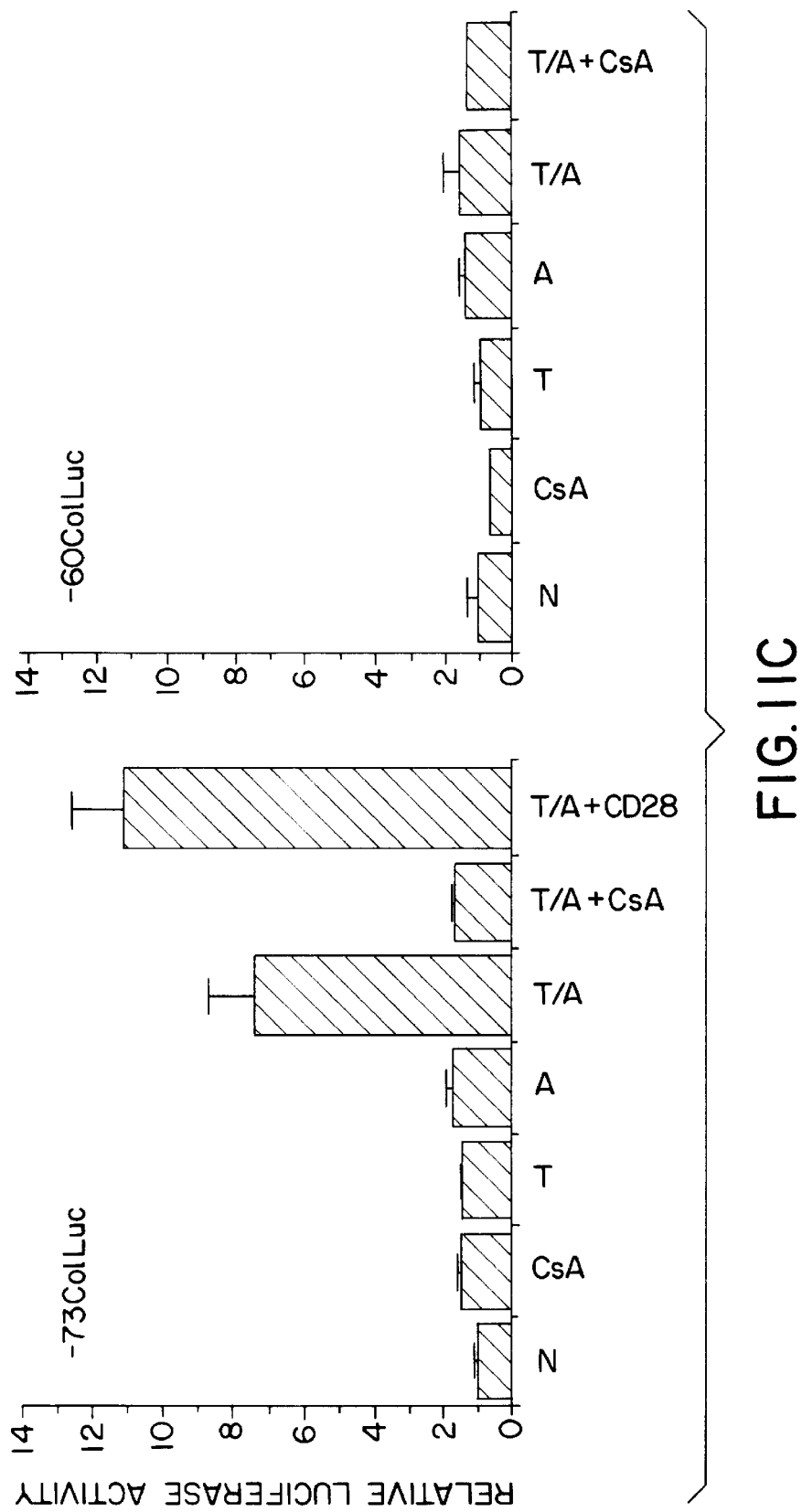

FIG. 11C shows Jurkat cells transfected with 10 g of either −73Col-LUC or −60Col-LUC reporter plasmids. 24 hours after transfection, the cells were aliquoted into 24 well plates and incubated for 9 hours with 50 ng/ml TPA, 1 μg/m; A23187 or 100 ng/ml CsA, either alone or in combination, as indicated. The cells were harvested and luciferase activity was determined. The results shown are averages of three experiments done in triplicates.

FIG. 12A shows Jurkat cells ($10^6$ cells per lane) transfected with 0.5 ug of a SRα-cJun expression vector and 24 hours later were labeled for 3 hours with $^{32}$P-orthophosphate (1 mCi/ml). After 15 minutes, treatment with 50 ng/ml TPA (T), 1 μg/ml A23187 (A) and 100 ng/ml CsA, either alone or in combination, as indicated, the cells were lysed in RIPA buffer and c-Jun was isolated by immunoprecipitation and analyzed by SDS-PAGE. The c-Jun bands are indicated.

FIG. 12B shows $2 \times 10^7$ Jurkat cells labeled for 3 hours with either $^{35}$S-methionine (900 μCi/ml) or $^{32}$P-orthophosphate (1 mCi/ml). After 15 minutes incubation with 50 ng/ml TPA+1 μg/ml A23178 (T/A) in the absence or presence of and 100 ng/ml CsA or no addition, as indicated, the cells were lysed in RIPA buffer and c-Jun isolated by immunoprecipitation and analyzed by SDS-PAGE. The c-Jun band is indicated.

Figure 12C:
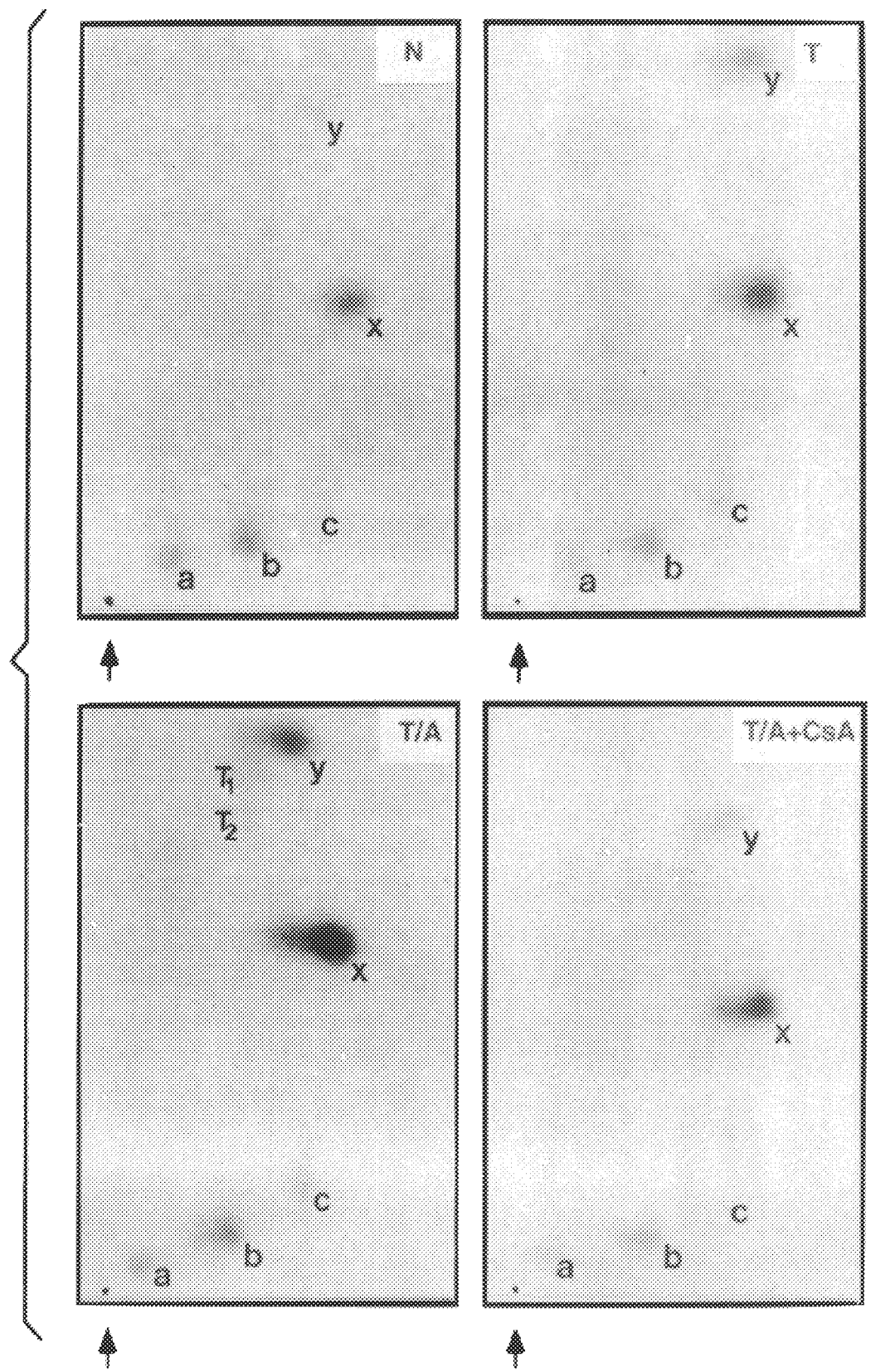

FIG. 12C shows all of the c-Jun specific protein bands shown in FIG. 12A isolated from equal numbers of cells excised from the gel and subjected to tryptic phosphopeptide mapping. Shown is a typical result (this experiment was repeated at least three times). N-nonstimulated cells; T-cells treated with 50 ng/ml TPA; T/A: cells treated with 50 ng/ml TPA and 1 μg/ml A23187; T/A+CsA: cells treated with T/A and 100 ng/ml CsA. a,b,c,x and y correspond to the various tryptic phosphopeptides of c-Jun, previously described by Boyle, et al., (Cell, 64:573–584, 1991) and Smeal, et al., (Nature, 354:494–496, 1991). T1 and T2 correspond to the minor phosphorylation sites; Thr91, 93 and 95 (Hibi, et al., Genes & Dev., 7:000, 1993).

Figure 13A:
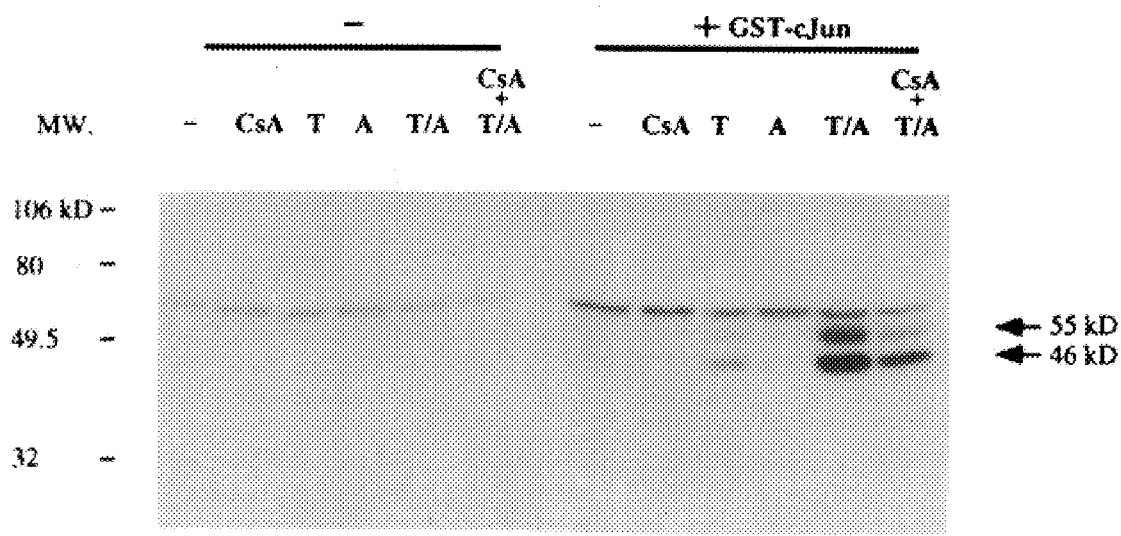

FIG. 13A shows whole cell extracts (WCE) of Jurkat cells incubated with TPA (T, 50 ng/ml), A23187 (A, 1 μg/ml) or CsA (100 ng/ml) for 15 minutes, alone or in combination, and separated by SDS-PAGE (100 μg protein/lane) on gels that were cast in the absence or presence of GST-cJun (1-223). The gels were subjected to renaturation protocol and incubated in kinase buffer containing γ-$^{32}$P-ATP. The protein bands corresponding to the 55 kD and 46 kD forms of JNK are indicated.

Figures 13B, 13C:
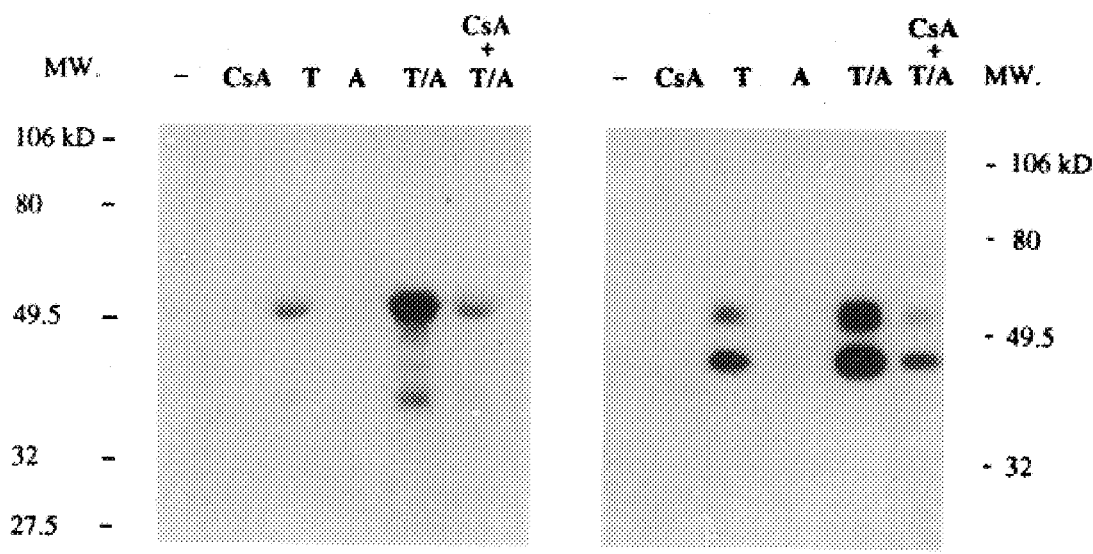

FIG. 13B shows WCE (50 μg) of Jurkat cells treated as described above were incubated with 5 μl of GSH agarose beads coated with 10 μg GST-cJun (1-223) for 12 hours at 4° C. After extensive washing, the beads were incubated in kinase buffer containing γ-$^{32}$P-ATP for 20 minutes at 30° C., after which the proteins were dissociated by incubation in SDS sample buffer and separated by SDS-PAGE. The 49 kD band corresponds to GST-cJun (1-223).

FIG. 13C shows WCE (200 μg) of Jurkat cells treated as described in FIG. 13A and incubated with GST-cJun(1-223) -GSH agarose beads. The bound fraction was eluted in SDS sample buffer and separated by SDS-PAGE on a gel containing GST-cJun(1-223). The gel was renatured and incubated in kinase buffer containing γ-$^{32}$P-ATP to label the JNK polypeptides.

Figure 14:
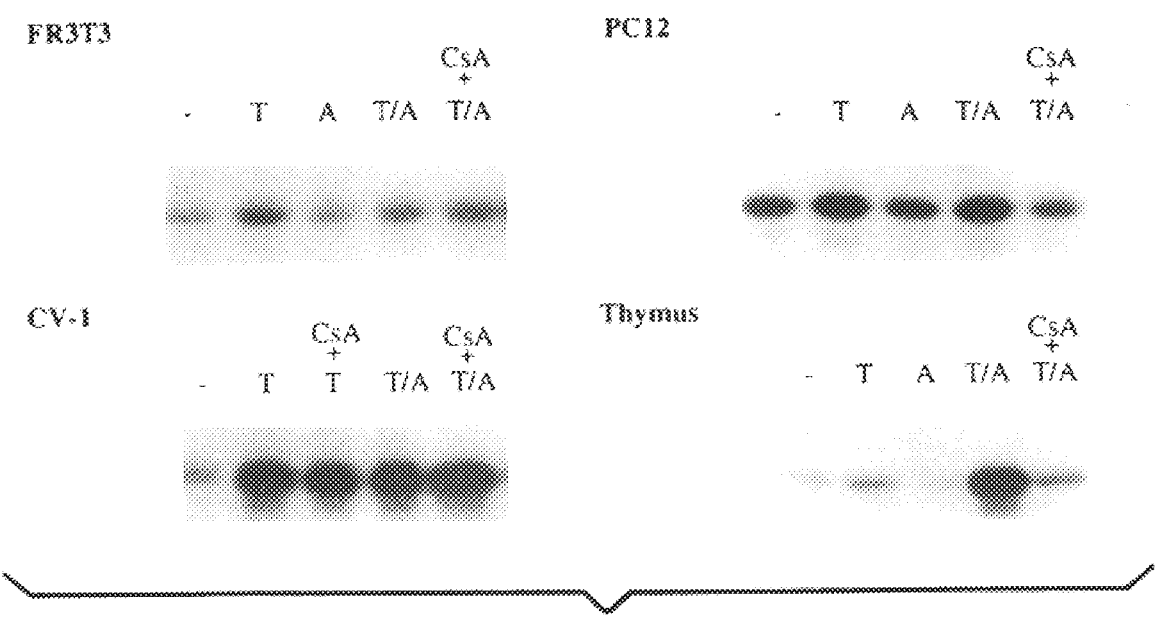
Figure 15A:
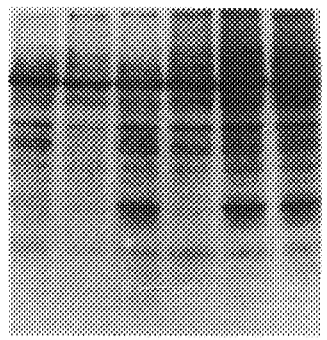
Figure 15C:
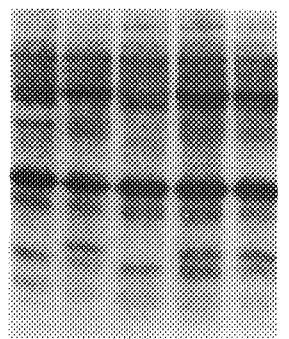
Figure 15B:
Figure 15D:

FIG. 14 shows a phosphorylation assay of cultures of FR3T3, CV-1, PC12 and mouse thymocytes were incubated for 15 minutes in the presence of TPA (50 ng/ml, T), A23817 (1 μg/ml, A) and/or CsA (100 ng/ml), as indicated. WCE prepared from $2–4 \times 10^5$ cells for the established cell lines and $1.5 \times 10^6$ cells for primary thymocytes were incubated with GSTcJun(1-223)-GSH agarose beads. After washing, JNK activity was determined by solid-state phosphorylation assay.

FIG. 15 shows WCE (5 ug) of Jurkat (panel A) or mouse thymocytes (panel C) incubated with 1 μg of kinase-defective ERK1 in kinase buffer containing γ-$^{32}$P-ATP for 20 minutes. The phosphorylated proteins were separated by SDS-PAGE and the band corresponding to the mutant ERK1 is indicated. WCE (20 μg) of Jurkat (panel A) or mouse thymocytes (panel C) that were treated as described above were immunoprecipitated with anti-ERK antibodies. The immune complexes were washed and incubated in kinase buffer containing γ-$^{32}$P-ATP and 2 μg MBP for 15 minutes at 30° C. The phosphorylated proteins were separated by SDS-PAGE. The band corresponding to phosphorylated MBP is indicated in panels B and D.

FIG. 16A shows Jurkat cells (1×10$^7$) incubated for 15 minutes with either normal mouse serum, 1 μg/ml anti-CD3 and/or 2 μg/ml anti-CD28, in the absence or presence of 100 ng/ml CsA, as indicated. WCE were prepared and 100 μg samples were analyzed for JNK activation using an in-gel kinase assay.

FIG. 16B shows WCE (50 μg) of Jurkat cells treated as described for FIG. 16A incubated with GSTcJun(1-223)-GSH agarose beads and assayed for JNK activity using the solid-state kinase assay. The same WCE (20 μg) were immunoprecipitated with anti-ERK2 antibodies and assayed for MBP-kinase activity.

FIG. 16C shows WCE (50 μg) of Jurkat cells treated as described in FIG. 16A with various stimuli alone or their combinations were incubated with GSTcJun(1-223)-GSH agarose beads and assayed for JNK activity using solid-state kinase assay. The same samples (20 μg) were also assayed for MBP-kinase activity as described in FIG. 16B.

Figure 17A:
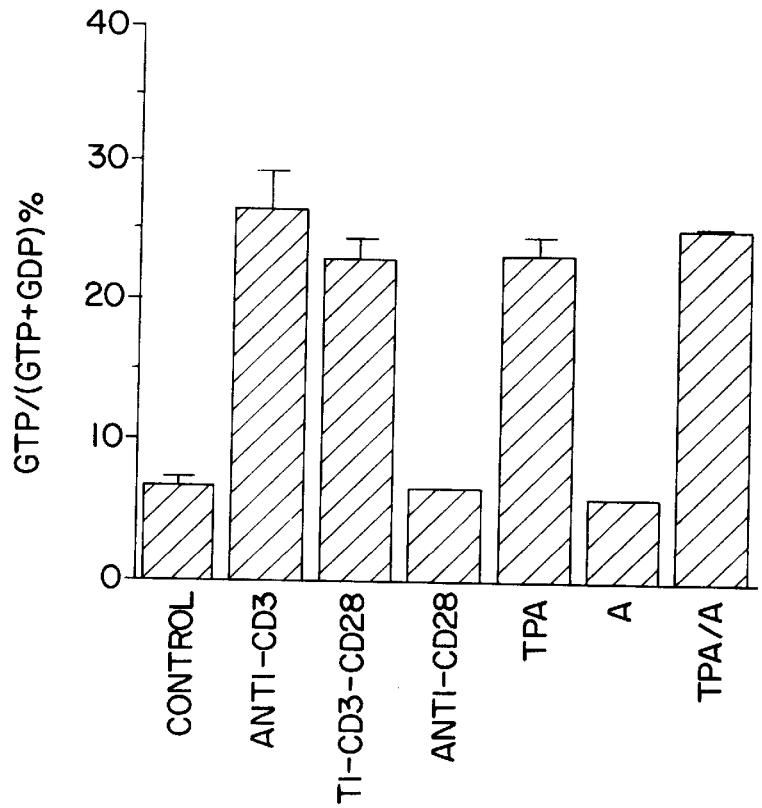

FIG. 17A shows Jurkat cells (2×10$^6$ cells per point) labeled with 0.4 mCi of $^{32}$P-orthophosphate for 3 hours and incubated with nonspecific antibody (1 μg/ml mouse IgG; control), 1 μg/ml anti-CD3, 2 μg/ml anti-CD28, 10 ng/ml TPA or 500 ng/ml A23187 (A), as indicated. After 2 minutes, the cells were harvested, lysed and Ha-Ras was isolated by immunoprecipitation. The guanine nucleotide bound to Ha-Ras was extracted, separated by thin layer chromatography and quantitiated. The values shown represent the averages of two separate experiments done in duplicates.

Figure 17B:
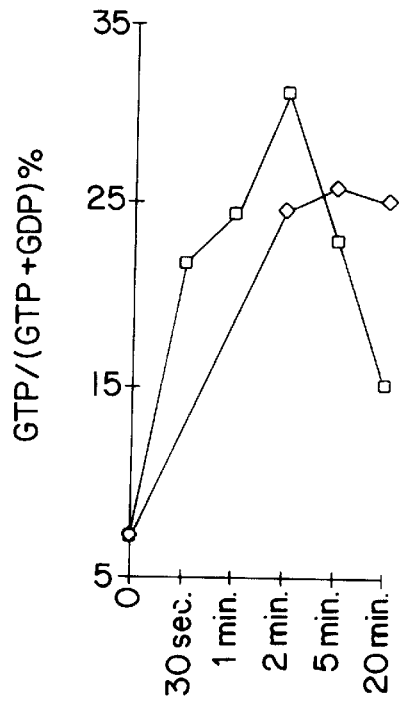

FIG. 17B shows Jurkat cells labeled with $^{32}$P-orthophosphate and stimulated with either TPA or anti-CD3. At the indicated time points, the cells were harvested and the GTP content of Ha-Ras was determined.

DETAILED DESCRIPTION OF THE INVENTION

The present invention provides a novel protein kinase (JNK) which binds to a well-defined region of the c-Jun proto-oncoprotein and phosphorylates two sites within its activation domain. The phosphorylation of these sites increases the ability of c-Jun to stimulate transcription and mediate oncogenic transformation.

The activity of c-Jun is regulated by phosphorylation. Various stimuli, including transforming oncogenes and UV light, induce the phosphorylation of serines 63 and 73 in c-Jun's N-terminal activation domain, thereby potentiating its transactivation function. The invention relates to an isolated polypeptide characterized by having a molecular weight of 46 kD as determined by reducing SDS-PAGE, having serine and threonine kinase activity and capable of phosphorylating the c-Jun N-terminal activation domain. This protein is referred to JNK1. In addition, a second JNK protein (55 kD) referred to as JNK2, is described.

The term "isolated" means any JNK polypeptide of the present invention, or any gene encoding a JNK polypeptide, which is essentially free of other polypeptides or genes, respectively, or of other contaminants with which the JNK polypeptide or gene might normally be found in nature.

The invention includes a functional polypeptide, JNK, and functional fragments thereof. As used herein, the term "functional polypeptide" refers to a polypeptide which possesses a biological function or activity which is identified through a defined functional assay and which is associated with a particular biologic, morphologic, or phenotypic alteration in the cell. The biological function, for example, can vary from a polypeptide fragment as small as an epitope to which an antibody molecule can bind to a large polypeptide which is capable of participating in the characteristic induction or programming of phenotypic changes within a cell. An enzymatically functional polypeptide or fragment of JNK possesses c-Jun N-terminal activation domain kinase activity. A "functional polynucleotide" denotes a polynucleotide which encodes a functional polypeptide as described herein.

Minor modifications of the JNK primary amino acid sequence may result in proteins which have substantially equivalent activity as compared to the JNK polypeptide described herein. Such modifications may be deliberate, as by site-directed mutagenesis, or may be spontaneous. All of the polypeptides produced by these modifications are included herein as long as the kinase activity of JNK is present. Further, deletion of one or more amino acids can also result in a modification of the structure of the resultant molecule without significantly altering its kinase activity. This can lead to the development of a smaller active molecule which would have broader utility. For example, it is possible to remove amino or carboxy terminal amino acids which may not be required for JNK kinase activity.

The JNK polypeptide of the invention also includes conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention also provides a synthetic peptide which binds to the c-Jun N-terminal kinase, JNK. The amino acid sequence of SEQ ID NO: 1, and conservative variations, comprises the synthetic peptide of the invention. This sequence represents amino acids 33–79 of c-Jun polypeptide (Angel, et al., Nature, 332(6160):166, 1988) As used herein, the term "synthetic peptide" denotes a peptide which does not comprise an entire naturally occurring protein molecule. The peptide is "synthetic" in that it may be produced by human intervention using such techniques as chemical synthesis, recombinant genetic techniques, or fragmentation of whole antigen or the like.

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al., Current Protocols in Immunology, Wiley Interscience, 1991, Unit 9). Peptides of the invention can also be synthesized by the well known solid phase peptide synthesis methods described Merrifield, *J. Am. Chem. Soc.,* 85:2149, 1962), and Stewart and Young, *Solid Phase Peptides Synthesis,* (Freeman, San Francisco, 1969, pp.27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The invention also provides polynucleotides which encode the JNK polypeptide of the invention and the synthetic peptide of SEQ ID NO: 1. As used herein, "polynucleotide" refers to a polymer of deoxyribonucleotides or ribonucleotides, in the form of a separate fragment or as a component of a larger construct. DNA encoding the polypeptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research,* 9:879, 1981).

The development of specific DNA sequences encoding JNK can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., *Nucl. Acid Res.* 11:2325, 1983).

A cDNA expression library, such as lambda gt11, can be screened indirectly for JNK polypeptide having at least one epitope, using antibodies specific for JNK. Such antibodies can be either polyclonally or monoclonally derived and used to detect expression product indicative of the presence of JNK cDNA.

A polynucleotide sequence can be deduced from the genetic code, however, the degeneracy of the code must be taken into account. Polynucleotides of the invention include sequences which are degenerate as a result of the genetic code. The polynucleotides of the invention include sequences that are degenerate as a result of the genetic code. There are 20 natural amino acids, most of which are specified by more than one codon. Therefore, as long as the amino acid sequence of JNK results in a functional polypeptide (at least, in the case of the sense polynucleotide strand), all degenerate nucleotide. sequences are included in the invention.

The polynucleotide sequence for JNK also includes sequences complementary to the polynucleotide encoding JNK (antisense sequences). Antisense nucleic acids are DNA or RNA molecules that are complementary to at least a portion of a specific mRNA molecule (Weintraub, *Scientific American,* 262:40, 1990). The invention embraces all antisense polynucleotides capable of inhibiting production of JNK polypeptide. In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to cause problems than larger molecules when introduced into the target JNK-producing cell. The use of antisense methods to inhibit the translation of genes is well known in the art (Marcus-Sakura, *Anal.Biochem.,* 172:289, 1988).

In addition, ribozyme nucleotide sequences for JNK are included in the invention. Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med.Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The JNK polypeptides of the invention can also be used to produce antibodies which are immunoreactive or bind to epitopes of the JNK polypeptides. Antibodies of the invention also include antibodies which bind to the synthetic peptide in SEQ ID NO: 1. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256:495, 1975; *Current Protocols in Molecular Biology*, Ausubel, et al., ed., 1989).

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the JNK polypeptide of the invention can be prepared using an intact polypeptide or fragments containing small peptides of interest as the immunizing antigen. The polypeptide or a peptide such as Sequence ID No.1 used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, in the present invention, an anti-idiotype antibody produced from an antibody which binds to the synthetic peptide of the invention can bind to the site on JNK which binds to c-Jun, thereby preventing JNK from binding to and phosphorylating c-Jun.

Polynucleotide sequences encoding the polypeptide or the synthetic peptide (SEQ ID NO: 1) of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

DNA sequences encoding the polypeptides can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

In the present invention, the JNK polynucleotide sequences may be inserted into a recombinant expression vector. The term "recombinant expression vector" refers to a plasmid, virus or other vehicle known in the art that has been manipulated by insertion or incorporation of the genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyltransferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoribosyltransferse (XGPRT, gpt).

Transformation of a host cell with recombinant DNA may be carried out by conventional techniques which are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Examples of mammalian host cells include COS, BHK, 293, and CHO cells.

Isolation and purification of host cell expressed polypeptide, or fragments thereof, provided by the invention, may be carried out by conventional means including preparative chromatography and immunological separations involving monoclonal or polyclonal antibodies.

The JNK protein kinase of the invention is useful in a screening method for identifying compounds or compositions which affect the activity of the kinase. Thus, in another embodiment, the invention provides a method for identifying a composition which affects a c-Jun N-terminal kinase comprising incubating the components, which include the composition to be tested and the kinase or a polynucleotide encoding the kinase, under conditions sufficient to allow the components to interact, then subsequently measuring the effect the composition has on kinase activity-or on the polynucleotide encoding the kinase. The observed effect on the kinase may be either inhibitory or stimulatory. For example, the increase or decrease of kinase activity can be measured by adding a radioactive compound to the mixture of components, such as 32P-ATP, and observing radioactive incorporation into c-Jun or other suitable substrate for JNK, to determine whether the compound inhibits or stimulates protein kinase activity. A polynucleotide encoding the kinase may be inserted into an expression vector and the effect of a composition on transcription of the kinase can be measured, for example, by Northern blot analysis.

In another embodiment, the invention provides a method of treating a cell proliferative disorder associated with JNK comprising administering to a subject with the disorder a therapeutically effective amount of reagent which modulates kinase activity. The term "therapeutically effective" means that the amount of monoclonal antibody or antisense nucleotide, for example, which is used, is of sufficient quantity to ameliorate the JNK associated disorder. The term "cell-proliferative disorder" denotes malignant as well as non-malignant cell populations which morphologically often appear to differ from the surrounding tissue. For example, the method may be useful in treating malignancies of the various organ systems, such as lung, breast, lymphoid, gastrointestinal, and genito-urinary tract as well as adenocarcinomas which include malignancies such as most colon cancers, renal-cell carcinoma, prostate cancer, non-small cell carcinoma of the lung, cancer of the small intestine and cancer of the esophagus.

The method is also useful in treating non-malignant or immunological-related cell-proliferative diseases such as psoriasis, pemphigus vulgaris, Behcet's syndrome, acute respiratory distress syndrome (ARDS), ischemic heart disease, post-dialysis syndrome, leukemia, rheumatoid arthritis, acquired immune deficiency syndrome, vasculitis, septic shock and other types of acute inflammation, and lipid histiocytosis. Especially preferred are immunopathological disorders. Essentially, any disorder which is etiologically linked to JNK kinase activity would be considered susceptible to treatment.

Treatment includes administration of a reagent which modulates JNK kinase activity. The term "modulate" envisions the suppression of expression of JNK when it is over-expressed, or augmentation of JNK expression when it is under-expressed. It also envisions suppression of phosphorylation of c-Jun, for example, by using the peptide of SEQ ID NO:1 as a competitive inhibitor of the natural c-Jun binding site in a cell. When a cell proliferative disorder is associated with JNK overexpression, such suppressive reagents as antisense JNK polynucleotide sequence or JNK binding antibody can be introduced to a cell. In addition, an anti-idiotype antibody which binds to a monoclonal antibody which binds a peptide of the invention may also be used in the therapeutic method of the invention. Alternatively, when a cell proliferative disorder is associated with underexpression or expression of a mutant JNK polypeptide, a sense polynucleotide sequence (the DNA coding strand) or JNK polypeptide can be introduced into the cell.

The antibodies of the invention can be administered parenterally by injection or by gradual infusion over time. The monoclonal antibodies of the invention can be administered intravenously, intraperitoneally, intramuscularly, subcutaneously, intracavity, or transdermally.

Preparations for parenteral administration of a peptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Polynucleotide sequences, including antisense sequences, can be therapeutically administered by various techniques known to those of skill in the art. Such therapy would achieve its therapeutic effect by introduction of the JNK polynucleotide, into cells of animals having the proliferative disorder. Delivery of JNK polynucleotide can be achieved using free polynucleotide or a recombinant expression vector such as a chimeric virus or a colloidal dispersion system. Especially preferred for therapeutic delivery of nucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a JNK sequence into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the JNK polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsitation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Another targeted delivery system for JNK polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The invention also provides a method for detecting a cell with JNK kinase activity or a cell proliferative disorder associated with JNK comprising contacting a cell component with c-Jun N-terminal kinase activity with a reagent which binds to the component and measuring the interaction of the reagent with the component. Such reagents can be used to measure relative levels of JNK expression compared to normal tissue. The cell component can be nucleic acid, such as DNA- or RNA, or protein. When the component is nucleic acid, the reagent is a nucleic acid probe or PCR primer. The interaction of a nucleic acid reagent with a nucleic acid encoding a polypeptide with c-Jun N-terminal kinase activity is typically measured using radioactive labels, however, other types of labels will be known to those of skill in the art. When the cell component is protein, the reagent is typically an antibody probe. The probes are directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

Preferably the probe for identification of a cell with JNK kinase activity is a c-Jun protein. JNK activity within a cell is measured by the amount of phosphorylation of the c-Jun protein probe. For example, the amount of JNK activity in a cell extract can be measured by mixing the extract with c-Jun protein and adding a radioactive compound such as $^{32}$P-ATP to the mixture of components. The amount of radioactivity that is incorporated into the c-Jun probe is determined, for example by SDS-PAGE, and compared to a cell control containing c-Jun and a normal level of JNK kinase activity.

The c-Jun substrate can be immobilized onto a 96 well microtiter dish and extracts from treated cells added to the wells. The wells are then washed and an appropriate buffer containing $^{32}$P-ATP is added to the wells. The phosphorylation reaction proceeds for about 15 minutes and the wells are washed and counted. Modifications of the assay include immobilizing the substrate using beads or magnetic particles and non-radioactive procedures to measure the substrate phosphorylation, such as using monoclonal antibodies and a detection system (e.g., biotinilated antibodies and avidin peroxidase reaction).

The Jun protein used in the method of detection of the JNK kinase described above may exist as a single protein unit or a fusion protein. The fusion protein preferably consists of c-Jun and glutathione-S-transferase (GST) as a carrier protein. The c-jun nucleotide sequence is cloned 3' to the carrier protein in an expression vector, such as pGEX or such derivatives as pGEX2T or pGEX3X, the gene is expressed, the cells are lysed, and the extract is poured over a column containing a resin or mixed directly with a resin to which the carrier protein binds. When GST is the carrier, a glutathione (GSH) resin is used. When maltose-binding protein (MBP) is the carrier, an amylose resin is used. Other carrier proteins and the appropriate binding resin will be known to those of skill in the art.

The materials of the invention are ideally suited for the preparation of a kit. The kit is useful for the detection of the level of a c-Jun N-terminal kinase comprising an antibody which binds a c-Jun N-terminal kinase or a nucleic acid probe which hybridizes to JNK nucleotide, the kit comprising a carrier means being compartmentalized to receive in close confinement therein one or more containers such as vials, tubes, and the like, each of the container means comprising one of the separate elements to be used in the assay. For example, one of the container means may comprise a monoclonal antibody of the invention which is, or can be, detectably labelled. The kit may also have containers containing buffer(s) and/or a container comprising a reporter-means (for example, a biotin-binding protein, such as avidin or streptavidin) bound to a reporter molecule (for example, an enzymatic or fluorescent label).

The following examples are intended to illustrate but not limit the invention. While they are typical of those that might be used, other procedures known to those skilled in the art may alternatively be used.

EXAMPLE 1

PLASMIDS AND EXPRESSION OF GST FUSION PROTEINS

The glutathione-S-transferase (GST)-cJun expression vector, pGEX2T-cJun(wt), was constructed by inserting a filled-in BspHI-PstI fragment (encoding AA 1-223) from RSV-cJun(BspHI) into the SmaI site of pGEX2T (Pharmacia). RSV-cJun(BspHI) was constructed by changing the translation initiation sequence CTATGA of RSV-cJun to TCATGA by site-directed mutagenesis. The GSTcJun(Ala63/67)(BspHI) expression vector was derived in the same manner from RSV-cJun(Ala63/73) (Smeal, et al., supra, 1991) and was used to construct pGEX2T-cJun (Ala 63/67). The various GSTcJun truncation mutants were constructed using the polymerase chain reaction (PCR) to amplify various portions of c-Jun coding region. The sequences of the primers are indicated below:

N-terminal primers: TCTGCAGGATCCCC ATGACTGCAAAGATGGAAACG (underlined codon: amino acid 1) (SEQ ID NO: 2); TCTGCAG-GATCCCCGACGATGCCCTCAACGCCTC (a.a. 11) (SEQ ID NO: 3); TCTGCAGGATCCCC GAGAGCGGACCTTATGGCTAC (a.a. 22) (SEQ ID NO: 4); TCTGCAGGATCCCC GCCGACCCAGTGGGGAGCCTG (a.a. 43) (SEQ ID NO: 5); TCTGCAGGATCCCC AAGAACTCGGACCTCCTCACC (a.a. 56) (SEQ ID NO: 6) C-terminal primers: TGAATTCTG CAGGCGCTCCAGCTCGGGCGA (a.a. 79) (SEQ ID NO: 7); and TGAATTCCTGCA GGTCGGCGTGGTGGTGATGTG (a.a. 93) (SEQ ID NO: 8).

The DNA fragments were amplified by using Pfu polymerase (Strategene, La Jolla, Calif.), digested with BamHI and PstI, and subcloned to BamHI, PstI sites of pBluescript SK+ (Strategene). The BamHI-EcoRI fragments were excised from pBluescript and subcloned to BamHI, PstI sites of pGEX3X (Pharmacia). Some constructs were made by inserting BamHI-AvaI fragments of the PCR products and the AvaI-EcoRI fragment of pGEX2T-cJun(wt) into BamHI, EcoRI sites of pGEX3X. pGEX3X-cJun(33-223) was constructed by inserting a XholI-EcoRI fragment into pGEX3X.

The v-Jun and chick c-Jun sequences were derived from RCAS VC-3 and RCAS CJ-3 respectively (Bos, et al., *Genes Dev.*, 4:1677, 1990). GSTfusion vectors for v-Jun and chicken c-Jun were constructed by inserting NcoI fragments of RCAS VC-3 and RCAS CJ-3 into NcoI site of pGEX-KG (Guan and Dixon, *Anal. Biochem.*, 192:262, 1989). The same fragments contain various portions of the c-Jun and v-Jun coding regions were cloned into pSG424, a GAL4 DNA binding domain expression vector (Sadowski and Ptashne, *Nucl. Acids Res.*, 17:753, 1989).

The GST fusion protein expression vectors were transformed into the XL1 -Blue or NM522 strains of *E. coli*. Protein induction and purification were performed as previously described (Smith and Johnson, *Gene*, 67:31, 1988). The amount of purified fusion protein was estimated by the Bio-Rad Protein Assay Kit. In some experiments GST fusion proteins were not eluted from the glutathione (GSH)-agarose beads and were retained on the beads for isolation of the c-Jun N-terminal kinase.

Cell Culture and Preparation of Cell Extracts

FR3T3, Ha-ras transformed FR3T3, HeLaS3 and QT6 cells were grown in Dulbecco's modified Eagle's Medium (DMEM) containing 10% fetal calf serum (FCS), 100 U/ml penicillin (Pc), and 100 µg/ml streptomycin (Sm). Jurkat, K562 and U937 cells were grown in RPMI 1640 supplemented with 10% FCS, 100 U/ml Pc, and 100 µg/ml Sm. F9 cells were grown in 45% DMEM, 45% Ham's F12, 10% FCS, 100 U/ml Pc and 100 µg/ml Sm. Nuclear and cytoplasmic extracts were prepared as described by Dignam, et al., (1983). To prepare whole cell extract (WCE), harvested cells were suspended in WCE buffer: 25 mM HEPES pH 7.7, 0.3M NaCl; 1.5 mM MgCl$_2$ 0.2 mM EDTA, 0.1% Triton X-100, 0.5 mM DTT, 20 mM β-glycerophosphate, 0.1 mM Na$_3$VO$_4$, 2 µg/ml leupeptin, 100 µg/ml PMSF. The cell suspension was rotated at 4° C. for 30 minutes and the extract was cleared by centrifugation at 10,000 xg for 10 minutes. Protein amount was estimated by Bio-Rad Protein Assay Kit.

Transfection Experiments

Transfection experiments were performed using RSV-cJun, RSV-vJun and GAL4-Jun, GAL4-vJun and Ha-Ras (Leu 61) expression vectors as previously described (Boyle, et al., supra, 1991; Binetruy, et al., supra, 1991; Smeal, et al., 10 supra, 1991). CAT activity was determined as described in Example 8 below. c-Jun and v-Jun protein expression and phosphorylation were analyzed as described by Smeal, et al., supra, 1991; Smeal, et al., *Mol. Cell Biol.*, 12:3507, 1992).

Protein Purification

GST-fusion proteins were purified by affinity chromatography on GSH-agarose as described (Smith, et al., *Gene*, 67:31–40, 1988). Purified MAP kinase (a mixture of ERK1 and ERK2) was obtained from Dr. M. Cobb (University of Texas Southwestern). JNK-46 was purified from UV-irradiated HeLa S3 cells by standard liquid chromatography. Epitope-tagged JNK was immunopurified from transiently transfected COS cells. Briefly, COS cells were solubilized with 20 mM Tris (pH 7.6), 0.5% NP-40, 250 mM NaCl, 3 mM β-glycerophosphate, 3 mM EDTA, 3 mM EGTA, 100 μM Na orthovanadate, 10 μg/ml leupeptin, 1 mM PMSF. JNK was isolated by immunoaffinity chromatography using the M2 monoclonal antibody bound to protein A-Sepharose. The beads were washed extensively with Buffer A (20 mM Hepes (ph 7.7), 50 mM NaCl, 0.1 mM EDTA, 0.05% Triton X-100). JNK was eluted from the column with 3M urea in Buffer A and the dialyzed against Buffer A with 10% glycerol.

EXAMPLE 2

KINASE ASSAYS

Solid Phase Kinase Assay

Cell extracts were diluted so that the final composition of the WCE buffer was 20 mM HEPES pH 7.7, 75 mM NaCl, 2.5 mM $MgCl_2$, 0.1 mM EDTA, 0.05% Triton X-100, 0.5 mM DTT, 20 mM β-glycerolphosphate, 0.1 mM $Na_3VO_4$, 2μg/ml leupeptin, 100 μg/ml PMSF. The extracts were mixed with 10 μl of GSH-agarose suspension (Sigma) to which 10 μg of either GST or GST-Jun fusion proteins were bound. The mixture was rotated at 4° C. for 3 hours in a microfuge tube and pelleted by centrifugation at 10,000×g for 20 sec. After 4×1 ml washes in HEPES binding buffer (20 mM HEPES pH 7.7, 50 mM NaCl, 2.5 mM $MgCl_2$, 0.1 mM EDTA, 0.05% Triton X-100), the pelleted beads were resuspended in 30 μl of kinase buffer (20 mM HEPES pH 7.6, 20 mM $MgCl_2$, 20 mM β-glycerolphosphate, 20 μM p-nitrophenyl phosphate, 0.1 mM $Na_3VO_4$, 2 mM DTT) containing 20 μM ATP and 5 μCi $\gamma$-$^{32}$P-ATP. After 20 minutes at 30° C. the reaction was terminated by washing with HEPES binding buffer. Phosphorylated proteins were eluted with 30 μl of 1.5×Laemili sample buffer and resolved on a 10% SDS polyacrylamide gel, followed by autoradiography. Quantitation of phosphate incorporated was determined by gel slicing and scintillation counting. Phosphorylated GST fusion proteins were eluted from gel slices and subjected to phosphopeptide mapping as described (Boyle, et al, supra, 1991).

In-Gel Kinase Assay

In-gel kinase assay was performed as described by Kameshita and Fujisawa, *Anal. Biochem.*, 183:1 39, (1989) with slight modifications. Briefly, c-Jun binding proteins were isolated from whole cell extracts by using GSH-agarose beads containing 80 μg GST-cJun as described above. Proteins were eluted in Laemli sample buffer and resolved on 10% SDS-polyacrylamide gel, which was polymerized in the absence or presence of GST-cJun (40 μg/ml). After electrophoresis, the gel was washed twice, 30 minutes each time with 100 ml of 20% 2-propanol, 50 mM HEPES pH 7.6 to remove SDS. After the gel was washed twice, 30 minutes each time, with 100 ml of buffer A (50 mM HEPES pH 7.6, 5 mM β-mercaptoethanol), it was incubated in 200 ml of 6M urea in buffer A at room temperature for 1 hr, followed by serial incubations in buffer A containing 0.05% Tween 20 and either 3M, 1.5M or 0.75M urea. After the gel was washed several times, 1 hr each time, with 100 ml of buffer A containing 0.05% Tween 20 at 4° C., it was incubated with kinase buffer containing 50 μM ATP and 5 μCi/ml $\gamma$-$^{32}$P-ATP at 30° C. for 1 hour. After the reaction, the gel was washed with 100 ml of 5% tricholoroacetic acid and 1% sodium pyrophosphate at room temperature several times, followed by drying and autoradiography.

EXAMPLE 3

BINDING OF A PROTEIN KINASE TO GST-cJun-GSH-AGAROSE BEADS

Figure 1:
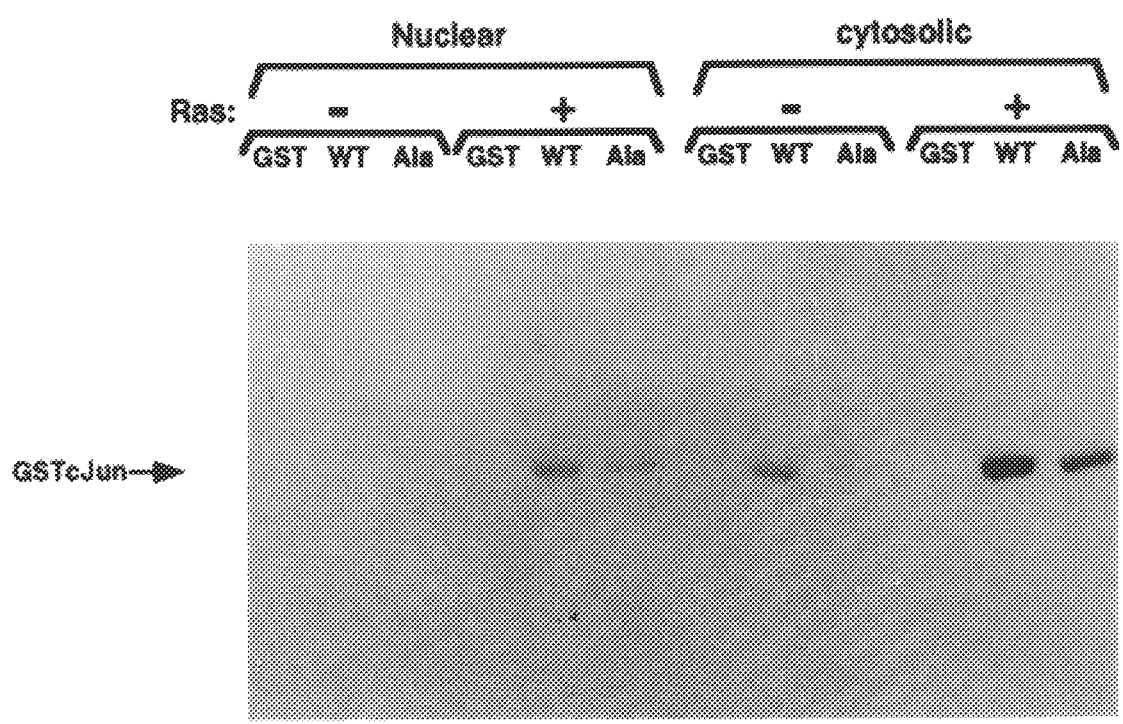
FIG. 1 shows an SDS-PAGE of nuclear and cytosolic extracts from FR3T3 (−) and Ha-ras-transformed FR3T3 (+)

The fusion protein, GSTcJun(wt), can bind through its GST moiety to glutathione (GSH)-agarose beads to generate an affinity matrix for identification of c-Jun binding proteins, which may include protein kinases. Ha-ras transformation of FR3T3 cells results in increased phosphorylation of c-Jun on Ser 63 and 73 (Binetruy, et al., supra, 1991; Smeal, et al., supra, 1991). Preliminary experiments indicated that transformed cells contained higher levels of c-Jun N-terminal kinase activity, while the levels of c-Jun C-terminal kinase activity remained unchanged. To develop a more convenient assay for characterizing the c-Jun N-terminal kinase activity, nuclear and cytoplasmic extracts of untransformed and transformed FR3T3 cells were mixed with GSTcJun(wt)-GSH-agarose beads. FRT3T3(−) and Ha-ras-transformed FR3T3(+) cells were kept in 0.5% FCS for 24 hours and harvested to prepare nuclear and cytosolic extracts. These extracts (prepared from equal number of cells) were mixed with GSH-agarose beads containing 10 μg of GST-cJun(wt), GSTcJun(Ala63/73) or GST. After a 3 hour incubation, the beads were spun down, washed 4-times and incubated in kinase buffer containing $\gamma$-$^{32}$P-ATP for 20 minutes at 30° C. The reaction was terminated by washing in SDS sample buffer. The eluted proteins were resolved by SDS-PAGE. The location of the GSTcJun fusion proteins is indicated in FIG. 1. Similar results were obtained when protein concentration rather than cell number (300 μg of cytosolic extract and an equivalent amount of nuclear extract) was used to normalize the amounts of extracts used in this assay. This procedure resulted in phosphorylation of GSTcJun(wt), suggesting that a protein kinase bound to it and phosphorylated it while attached to GSH-agarose (FIG. 1). On the other hand, no phosphorylation of GST bound to GSH-agarose could be detected by this assay.

The same experiment was repeated using a GSTcJun (Ala63/73) fusion protein, in which both the serine at position 63 and 73 were converted to alanines in order to identify a kinase that targets Ser 63 and 73 of c-Jun. Phosphorylation of this protein was considerably lower than that of GSTcJun(wt) (FIG. 1). These experiments confirmed the previous observations that the kinase activity affecting the N-terminal sites of c-Jun was elevated upon Has-ras transformation and are consistent with the differences in the extent of c-Jun N-terminal phosphorylation between transformed and untransformed cells detected by in vivo labelling (Binetruy, et al., supra, 1991; Smeal, et al., supra, 1991, 1992). The kinase activity detected by this solid-phase assay was present in both the cytosolic and the nuclear fractions and was several-fold more abundant in the cytosol on a per-cell basis. However, it is possible that some of the kinase leaked from the nuclei to the cytosol during the cell fractionation.

The solid-phase assay was used to examine N-terminal c-Jun kinase activity in other cell types. Exposure of HeLa cells to UV activates the Ha-Ras signalling pathway and results in a large increase in N-terminal phosphorylation of c-Jun (Devary, et al., Cell, 71:1081, 1992). Treatment of HeLa cells with the phorbol ester, TPA, on the other hand, has only a marginal effect on N-terminal phosphorylation of c-Jun (Boyle, et al., 1991). HeLa S3 cells were serum starved for 12 hours and were either left untreated, irradiated with UV light (40 J/m$^2$) or incubated with TPA (100 ng/ml). The cells were harvested at the indicated times (min) after UV or TPA exposure. Whole cell extracts (approximately 800 μg protein) isolated form equal numbers of cells were mixed with GSH-agarose beads containing 10 μg of either GST, GSTcJun(wt), or GSTcJun(Ala 63/73). After 3 hours incubation, followed by extensive washing, the solid state phosphorylation assay was performed as described above. After a 20 minute reaction, the proteins were dissociated in SDS sample buffer and resolved by SDS-PAGE.

Figure 2A:
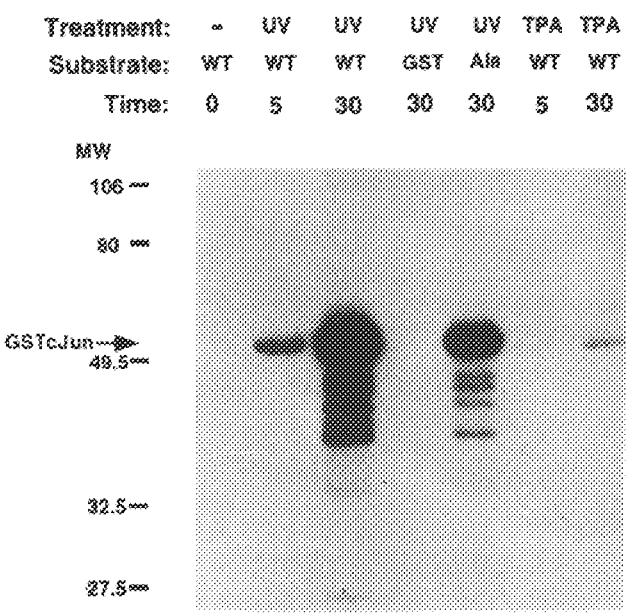

As shown in FIG. 2A, N-terminal c-Jun kinase activity was elevated within 5 minutes after UV irradiation and was 250-fold higher after 30 minutes than in unstimulated cells. The effect of TPA, however, was minor compared to that of UV. As found before, GSTcJun(wt) was more efficiently phosphorylated than GSTcJun(Ala63/73), whereas GST was not phosphorylated. These results are consistent with in vivo measurements of c-Jun phosphorylation (Boyle, et al, supra, 1991; Devary, et al., supra, 1992).

TPA treatment of Jurkat T cells, in contrast to HeLa cells, resulted in stimulation of c-Jun phosphorylation on Ser 63 and 73. Jurkat cells were serum starved for 2 hours and either left untreated or stimulated with TPA (50 ng/ml) for 10 or 30 minutes. Whole cell extracts prepared from 5×10$^6$ cells were mixed with GSH-agarose beads containing GST, GSTcJun(wt) or GSTcJun(Ala63/73). Phosphorylation of the GST proteins attached to the beads was performed as described above. The faster moving bands correspond to degradation products of the GSTcJun proteins.

Figure 2B:
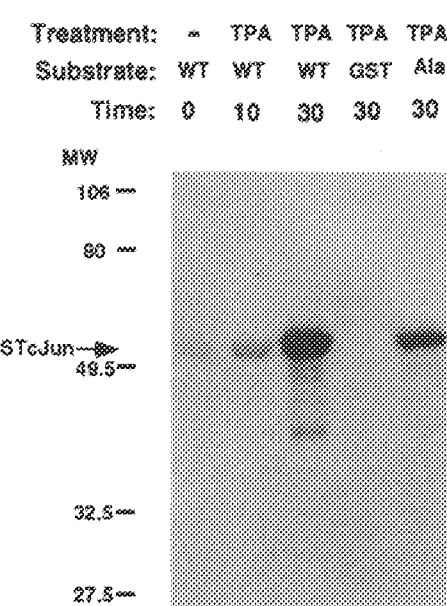

In Jurkat cells, unlike HeLa cells, the N-terminal kinase activity was found to be strongly activated by TPA (25-fold after 30 minutes) (FIG. 2B). This kinase also preferred GSTcJun(wt) over GSTcJun(Ala63/73) and did not bind to or phosphorylate the GST moiety. Collectively, these findings suggest that the kinase detected by the solid-phase assay phosphorylates c-Jun on Ser 63 and 73 and that its regulation parallels that of c-Jun N-terminal phosphorylation examined by in vivo labelling.

EXAMPLE 4

PHOSPHORYLATION OF SERINES 63 AND 73 BY BOUND KINASE, JNK

To determine the exact phosphoacceptor sites used by the kinase that binds to GSTcJun, the phosphorylated GSTcJun (wt) and GSTcJun(Ala63/73) proteins were subjected to two-dimensional tryptic phosphopeptide mapping. Whole cell extracts of Ha-ras-transformed FR3T3 cells (2.5 mg), UV irradiated HeLa cells (200 μg) or TPA-stimulated Jurkat cells (1.2 mg) were mixed with GSH-agarose beads, containing either GSTcJun(wt) or GSTcJun(Ala63/73). The GSTcJun proteins were phosphorylated as described above by the bound kinase, isolated by SDS-PAGE, excised from the gel, digested with trypsin and subjected to two-dimensional phosphopeptide mapping. The X, Y, T1, and T2 phosphopeptides are indicated. All the autoradiograms were exposed for the same length of time.

Figure 3A:
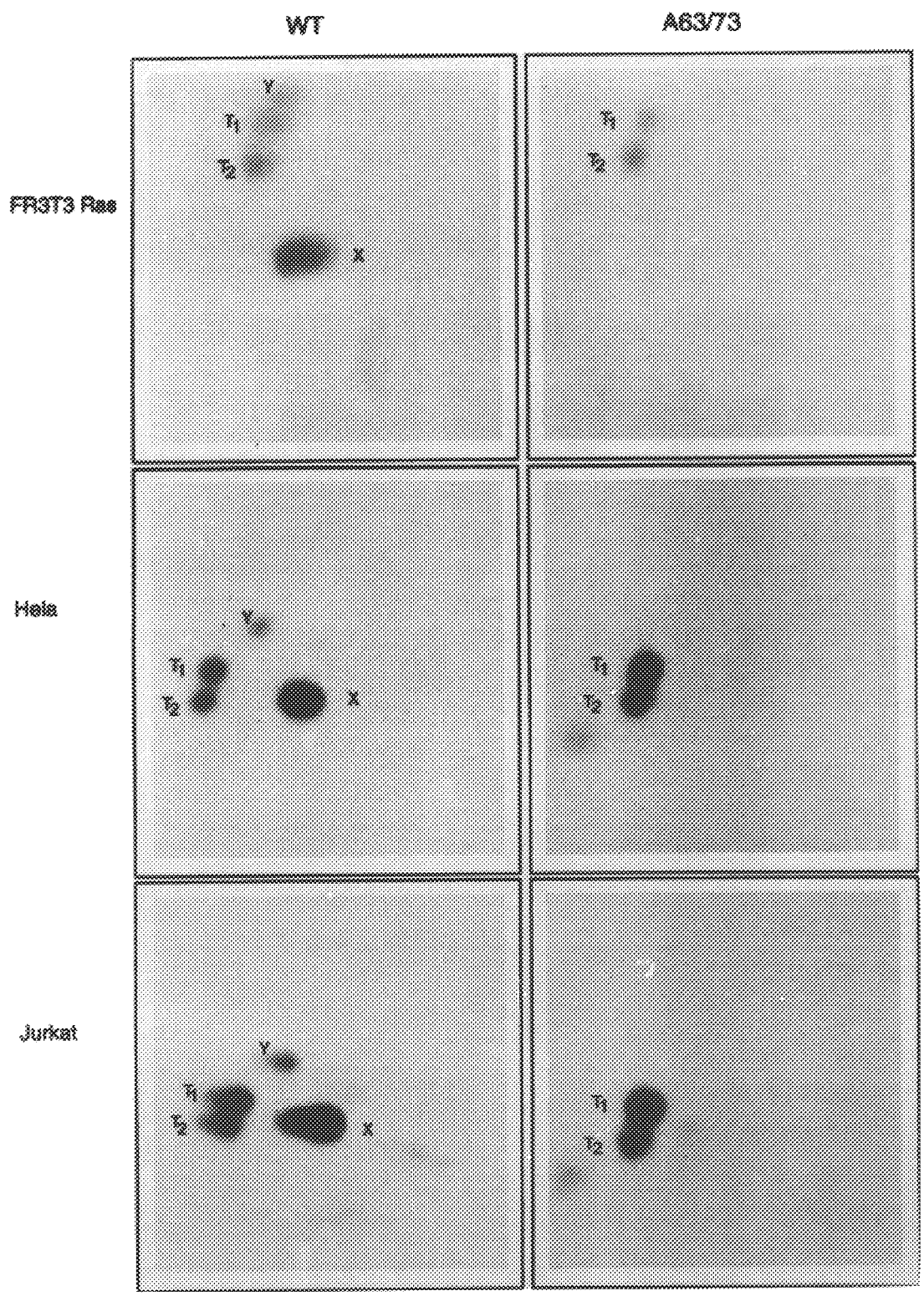

As shown in FIG. 3A, the kinases isolated from Ha-ras-transformed FR3T3 cells, UV-irradiated HeLa cells and TPA-stimulated Jurkat cells, phosphorylated GSTcJun on X, Y, and two other peptides, T1 and T2. X and Y correspond to phosphorylation of Ser-73-and Ser-63, respectively (Smeal, et al, supra, 1991) and were absent in digests of GSTcJun(A1a63/73), which contained higher relative levels of T1 and T2. Phosphoaminoacid analysis indicated that T1 and T2 contain only phosphothreonine. By deletion analysis these threonines were assigned to AA 91, 93 or 95 of c-Jun.

Figure 3B:
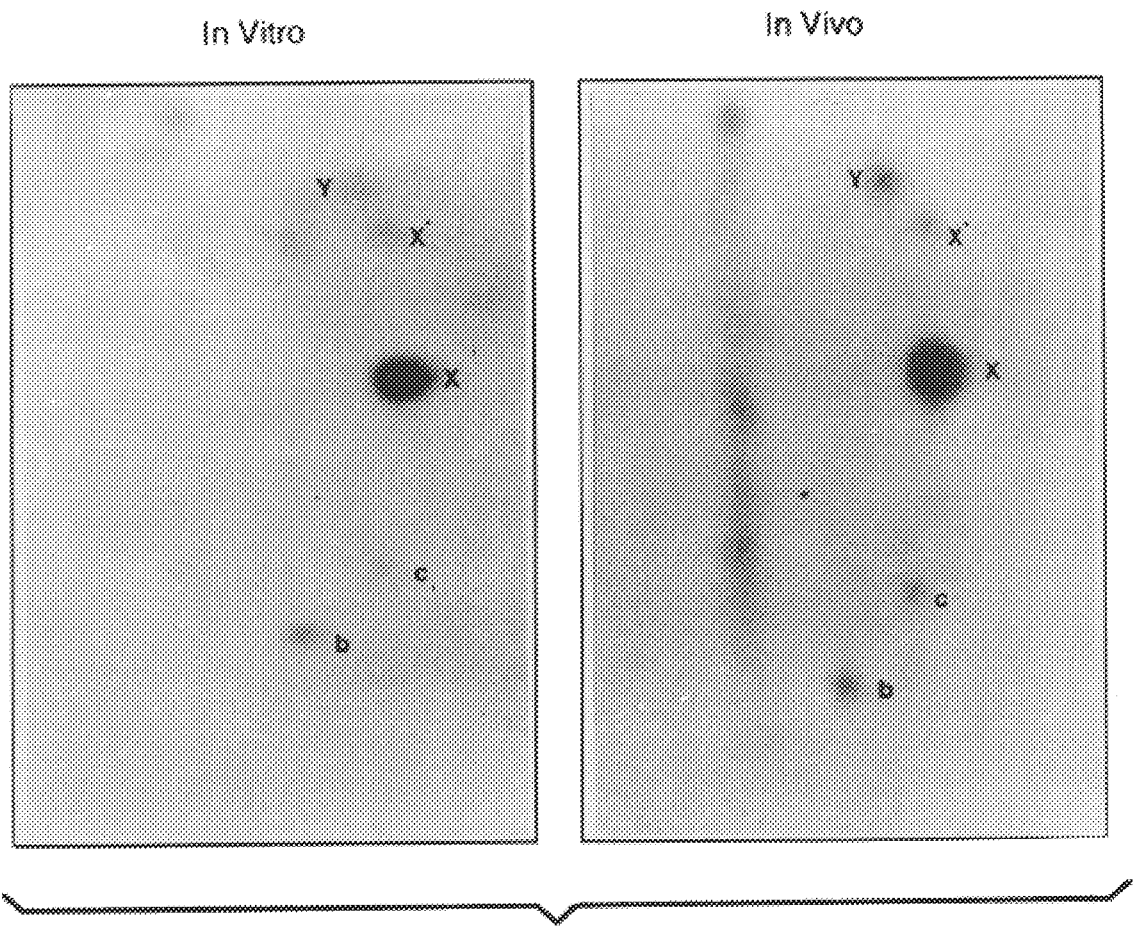

As described below, the kinase bound to GSTcJun was eluted from the beads and used to phosphorylate recombinant full-length c-Jun protein in solution (FIG. 3B). Recombinant c-Jun protein was phosphorylated in vitro by the c-Jun N-terminal kinase (JNK) eluted from GSTcJun(WT) -GSH-agarose beads. In addition, c-Jun was isolated by immuneprecipitation from $^{32}$P-labelled F9 cells that were cotransfected with c-Jun and Ha-Ras expression vectors (Smeal, et al., supra, 1991). Equal counts of each protein preparation were digested with trypsin and subjected to phosphopeptide mapping. The migration positions of the X, X' (a derivative of X generated by alkylation; Smeal, et al., supra, 1991) Y, b and c phosphopeptides are indicated.

As found in vivo, the bound kinase phosphorylated c-Jun mostly on Ser 73, followed by phosphorylation of Ser 63. In addition, the bound kinase activity phosphorylated c-Jun weakly on two of its C-terminal sites, resulting in appearance of phosphopeptides b and c. Since this is the first protein kinase that was detected with clear specificity for at least one of the N-terminal sites of c-Jun, it was named JNK, for cJun N-terminal protein-kinase.

EXAMPLE 5

BINDING OF JNK TO cJun

To examine the stability of the interaction between GSTc-Jun and JNK, extracts of TPA-stimulated Jurkat cells were incubated with GSTcJun(wt)-GSH-agarose beads. After extensive washing, the beads were subjected to elution with increasing concentrations of NaCl, urea, guanidine-HCl and SDS. Elution of JNK was examined by its ability to phosphorylate recombinant c-Jun in solution. GSTcJun(wt)-GSH-agarose beads were incubated for 3 hours with a whole cell extract of TPA-stimulated Jurkat cells and after four washes were subjected to elution in kinase buffer containing increasing concentrations of NaCl, urea, guanidine-HCl (in M) or SDS (in %)(FIG. 4). The eluted fractions (equal volumes) were dialyzed at 4° C. against kinase buffer containing 10% glycerol and no ATP and then incubated with recombinant c-Jun protein (250 ng) in the presence of 20 μM ATP and 5 μCi of γ-$^{32}$P-ATP for 20 minutes at 30° C. The amount of kinase remaining on the beads after the elution steps (R lanes) was determined by incubation of the isolated beads with kinase buffer in the presence of 20 μM ATP and 5 μCi γ-$^{32}$P-ATP for 20 minutes at 30° C. The phosphorylated proteins were analyzed by SDS-PAGE as described above and visualized by autoradiography. The migration positions of GSTcJun and c-Jun are indicated.

Surprisingly, JNK was found to bind GSTcJun rather tightly; only a small fraction of kinase activity was eluted by 0.5M NaCl and even after elution with 2M NaCl, most of the kinase remained on the beads (FIG. 4A). Approximately 50% of the bound kinase was eluted by 1M urea and the rest was efuted by 2M urea. Nearly complete elution was achieved by either 0.5M guanidine-HCl or 0.01% SDS. Under all of these elution conditions, GSTcJun(wt) was also partially eluted from the GSH-agarose beads. This suggests that the stability of the JNK:c-Jun complex is similar to that of the GST:GSH complex.

GSTcJun(wt) was covalently linked to GSH-agarose beads, using cyanogenbromide, and incubated with a whole cell extract of TPA-stimulated Jurkat cells. After extensive washing, part of the beads were eluted with kinase buffer-containing: no ATP (FIG. 4B, lane 2), 20 $\mu$M ATP (lane 3) or 50 $\mu$M ATP (lane 4). The eluted fractions (equal volumes) were incubated with recombinant c-Jun protein (500 ng) as a substrate and 5 $\mu$Ci $\gamma$-$^{32}$P-ATP for 30 minutes. In addition, the beads after elution with either kinase buffer alone (lane 1) or kinase buffer containing 50 $\mu$M ATP (lane 5) were incubated with c-Jun protein (500 ng) in the presence of 5 $\mu$Ci $\gamma$-$^{32}$P-ATP for 30 minutes. Phosphorylation of c-Jun (indicted by the arrow) was analyzed by SDS-PAGE and autoradiography.

Addition of exogenous c-Jun to kinase-loaded GSH-agarose beads to which GSTcJun was covalently linked results in its efficient phosphorylation (FIG. 4B, Lane 1). This suggests that after phosphorylating GSTcJun, JNK dissociates from it and phosphorylates exogenous c-Jun. In addition, incubation with kinase buffer containing ATP resulted in elution of JNK from the GSTcJun beads, as indicated by its ability to phosphorylate exogenous c-Jun (FIG. 4B, lanes 2–4). After incubation with 50 $\mu$M ATP less than 20% of the kinase remained on the beads (compare lanes 1 and 5, FIG. 4B).

EXAMPLE 6

JNK1 IS A 46 kD PROTEIN

An in-gel kinase assay was performed to determine the size of JNK. GSTcJun-GSH-agarose beads were incubated with a whole cell extract of TPA-stimulated Jurkat cells, washed extensively and the bound proteins were eluted in SDS sample buffer and separated on SDS-polyacrylamide gels that were polymerized in the absence (−) or presence (+) of GSTcJun(wt). After electrophoresis, the gel was incubated in 6M urea and subjected to renaturation as described in Example 1. The renatured gels were incubated in kinase buffer containing 50 $\mu$M ATP and 5 $\mu$Ci/ml $\gamma$-$^{32}$P-ATP for 1 hour at 30° C., washed, fixed, and visualized by autoradiography.

Figures 5A, 5B:
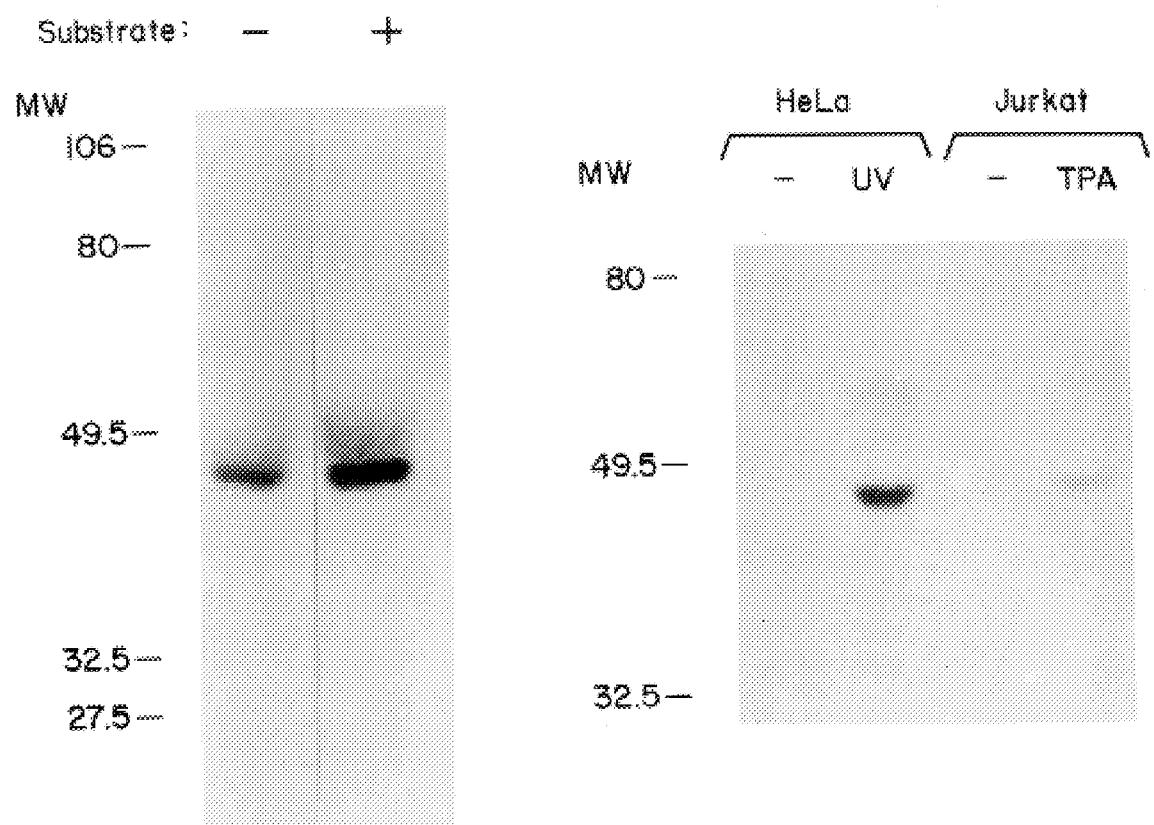

In both cases a protein band whose apparent molecular weight was 46 kD was phosphorylated (FIG. 5A). Phosphorylation was 2-fold more efficient in the presence of GSTc-Jun. This indicates that 46 kD protein band is either autophosphorylated JNK or a comigrating protein. No $^{32}$P-labelled protein was detected in eluates of GST-GSH-agarose beads.

The same in-gel kinase assay was used to demonstrate increased JNK activity upon TPA stimulation of Jurkat cells or UV irradiation of HeLa cells (FIG. 5B). GSTcJun-GSH-agarose beads were incubated with whole cell extracts of unstimulated or UV-stimulated HeLa cells and unstimulated or TPA-stimulated Jurkat cells. After washing, the bound proteins were eluted in SDS sample buffer and separated by SDS-PAGE. After renaturation, the gel was incubated in kinase buffer containing 50 $\mu$M ATP and 5 $\mu$Ci/ml $\gamma$-$^{32}$P-ATP and the phosphorylated proteins were visualized by autoradiography.

Figure 5C:
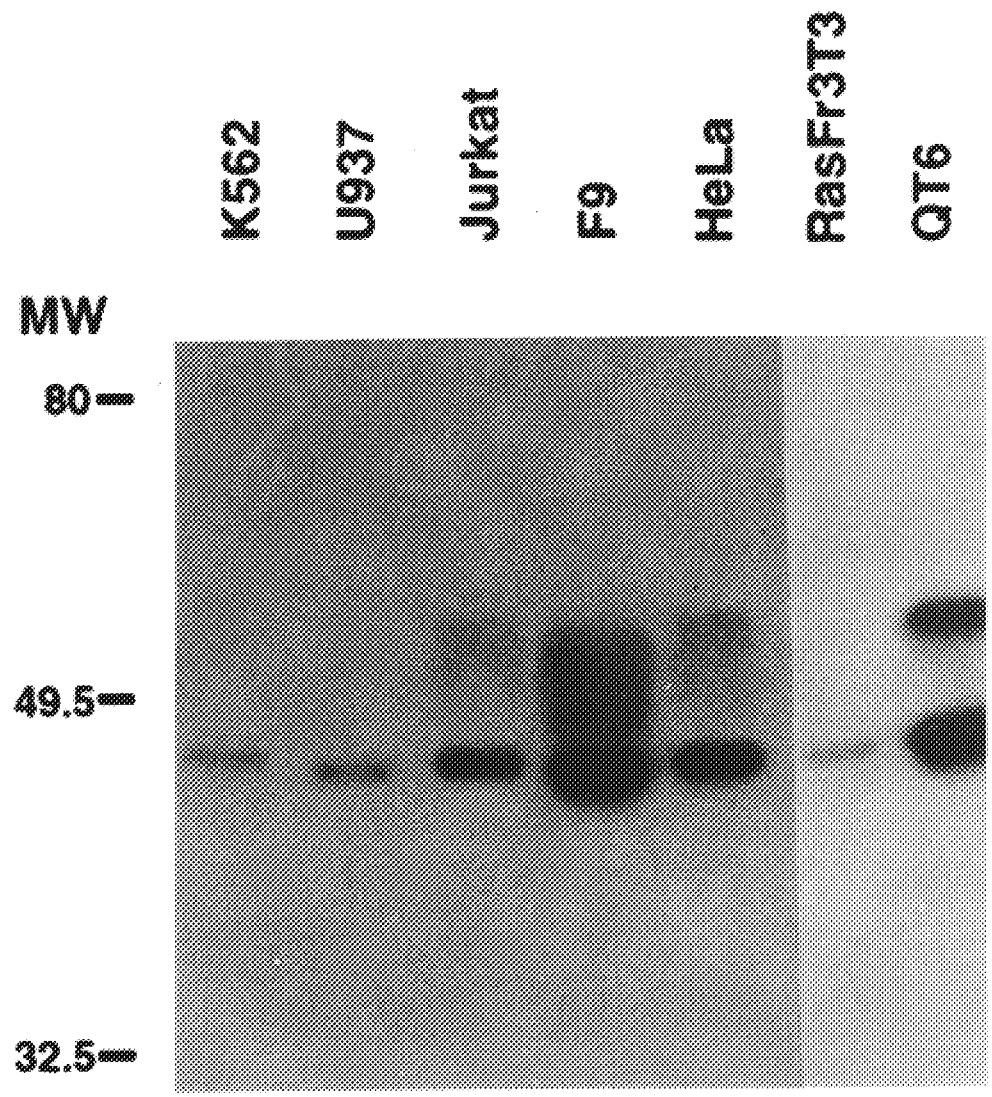

These results provide further evidence that the apparent molecular weight of JNK is 46 kD. To determine whether the same N-terminal c-Jun kinase is present in various cell types, the in-gel kinase assay was used to examine extracts of K562 human erythroleukemia cells, U937 human histiocytic leukemia cells, Jurkat cells, HeLa cells, F9 embryonal carcinoma cells, Ha-ras-trans-formed FR3T3 cells and QT6 quail fibroblasts. The HeLa, F9 and QT6 extracts were prepared form UV-irradiated cells and the U937 and Jurkat extracts were made from TPA-stimulated cells, while the K562 cells were not subjected to any special treatment. All cells contained a protein kinase that bound to GSTcJun and migrated around 46 kD (FIG. 5C). Some cells, especially QT6 cells, contained a second less abundant protein kinase species, migrating at about 55 kD. The activities of both kinases were induced by cell stimulation. GSTcJun(WT)-GSH-agarose beads were incubated with whole cell extracts of logarithmically growing K562 and Ha-ras transformed FR3T3 cells, TPA-stimulated Jurkat and U937 cells and UV-irradiated HeLa, F9 and QT6 cells. After washing, the bound proteins were eluted and analyzed by in-gel kinase assay as described above.

Further evidence that JNK is 46 kD in size was obtained by separating the GSTcJun-bound protein fraction of TPA-stimulated Jurkat cell extract by SDS-PAGE. PAGE. After elution and renaturation of the fractionated proteins, the molecular weight of the major protein kinase bound to GSTcJun, capable of specific phosphorylation of Ser 63 and 73, was determined to be 46 kD. Although the sizes of ERK1 and ERK2, 44 and 42 kD, respectively, are close to that of JNK, Western blot analysis, using an antiserum that reacts with both ERK's, indicates that the 46 kD JNK is not immunologically related to either of them. In addition, JNK is not immunologically related to Raf-1. In addition, a 55 kD polypeptide was identified as exhibiting JNK activity, however, the 46 kD appears to bind c-Jun more efficiently (Hibi, et al., *Genes Dev.*, 7:2135, 1993).

EXAMPLE 7

DELINEATION OF THE KINASE BINDING SITE

Deletion mutants of GSTcJun lacking either N-terminal or C-terminal sequences (FIG. 6A) were used to define the JNK binding site. GSTcJun fusion proteins containing various c-Jun sequences were expressed in *E. coli* and isolated by binding to GSH-agarose. The bound proteins were analyzed by SDS-PAGE and stained with Coomassie Blue. Numbers indicate the amino acids of c-Jun present in each fusion protein. The migration positions of the intact GST-fusion proteins are indicated by the dots. Faster migrating bands are degradation products.

These proteins were immobilized on GSH-agarose beads and incubated with an extract of UV-irradiated HeLa cells. Whole cell extracts of UV-irradiated HeLa S3 cells were mixed with GSH-agarose beads containing equal amounts of the various GST fusion proteins. After washing, the beads were incubated for 20 minutes in kinase buffer containing $\gamma$-$^{32}$P-ATP. The GST fusion proteins were eluted from the beads and analyzed by SDS-PAGE and autoradiography. The migration positions of the intact GST fusion proteins are indicated by the dots. After incubation with whole cell extracts of UV-irradiated HeLa cells and washing, part of the bound JNK fraction was eluted with 1M NaCl and examined for its ability to phosphorylate recombinant c-Jun (250 ng) in solution. Protein phosphorylation was analyzed by SDS-PAGE and autoradiography.

Binding of JNK was examined by its ability to phosphorylate the GSTcJun fusion proteins, all of which contained both Ser 63 and 73 (FIG. 6B). To exclude the possibility that any of the truncations may have altered the conformation of c-Jun affecting the presentation of its N-terminal phosphoacceptors without affecting JNK binding, the kinase eluted from these beads was examined for its ability to phosphorylate exogenous full-length c-Jun in solution (FIG. 6C). The results obtained by both assays indicated that removal of amino acids (AA) 1–21 had no effect on JNK binding. Removal of AA 1–32 decreased phosphorylation of GSTc-Jun but had only a small effect on kinase binding. Removal of AA 1–42, however, completely eliminated kinase binding. In contrast to the N-terminal truncations, the two C-terminal truncations, that were examined, had no effect on JNK binding and a GST fusion protein containing AA 1–79 of c-Jun exhibited full binding activity. Hence, AA 33–79 constitute the kinase binding site.

The JNK binding site encompasses the δ region, spanning AA 31–57 of c-Jun that are deleted in v-Jun (Vogt and Bos, 1990). To determine the involvement of the δ region in kinase binding, GST fusion proteins containing the N-terminal activation domain of chicken c-Jun (AA 1–144), or the equivalent region of v-Jun (FIG. 7A) were constructed. The activation domain (AA 1–144) of chicken (ch) c-Jun and the equivalent region of v-Jun were fused to GST and expressed in E. coli. GST fusion proteins were isolated on GSH-agarose beads and analyzed by SDS-PAGE and Coomassie Blue staining. The migration positions of the intact proteins are indicated by the dots. After loading these GST fusion proteins onto GSH-agarose the kinase binding assays were performed as described above.

Extracts of TPA-activated Jurkat cells were incubated with GSH-agarose beads containing GST, GSTcJun(Ch) or GSTvJun. After washing, the beads were incubated in kinase buffer containing $\gamma$-$^{32}$P-ATP and the phosphorylated GST fusion protein were analyzed as described for FIG. 6. The bound protein fraction was eluted from the GSTcJun(Ch) and GSTvJun beads and analyzed for its ability to phosphorylate c-Jun in solution, as described for FIG. 6. While chicken GSTcJun bound the kinase as efficiently as human GSTcJun, GSTvJun was defective in-JNK binding (FIG. 7B, C).

EXAMPLE 8

JNK BINDING IS REQUIRED FOR HA-RAS AND UV RESPONSIVENESS

Figure 8A:
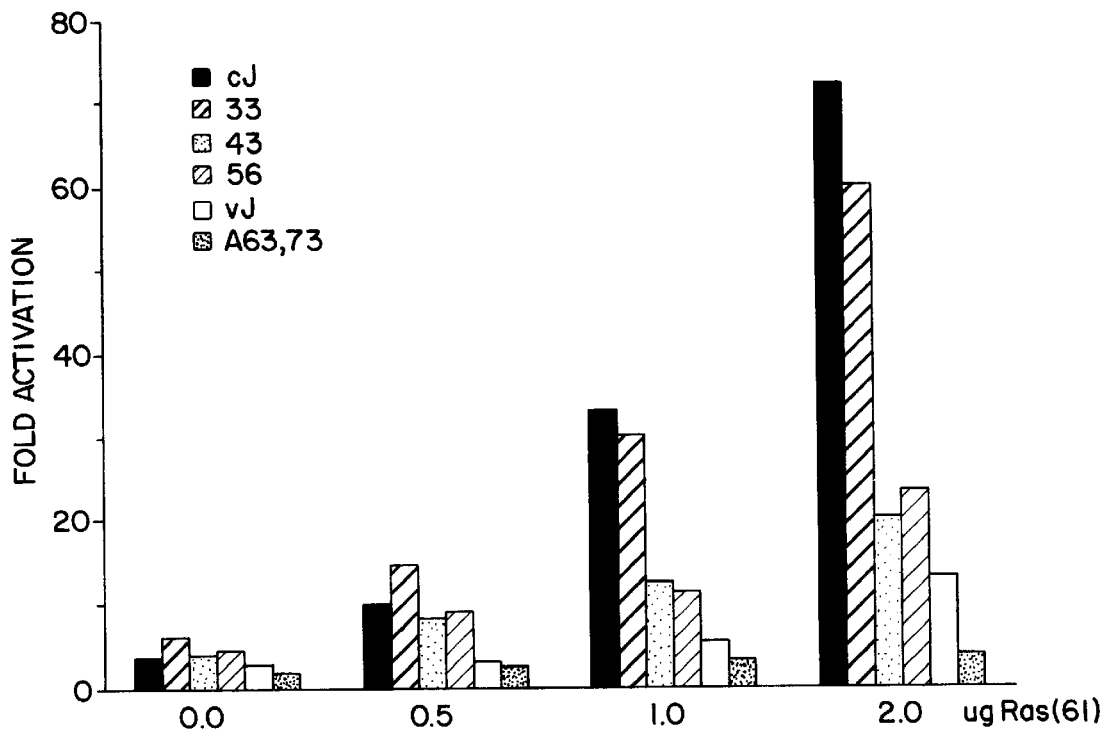

Phosphorylation of Ser 63 and 73 is necessary for potentiation of c-Jun mediated transactivation by Ha-Ras (Smeal, et al., supra, 1991). If binding of JNK has any role in this response, mutations that decrease kinase binding in vitro should attenuate the stimulation of c-Jun activity by Ha-Ras in vivo. This relationship was examined by cotransfection assays. Expression vectors were constructed to express chimeric GAL4-cJun and GAL4-vJun proteins, that consist of the DNA binding domain of the yeast activator GAL4 (Sadowski and Ptashne, 1989) and N-terminal sequences of c-Jun or v-Jun. The ability of these chimeras to activate the GAL4-dependent reporter 5×GAL4-Elb-CAT (Lillie and Green, 1989) was examined in the absence or presence of a cotransfected Ha-Ras expression vector (FIG. 8A). F9 cells were cotransfected with 1.0 µg of expression vector encoding the indicated GAL4-cJun chimeric proteins containing various portions of the c-Jun activation domain [cJ=AA1-223; 33-AA33-223; 56=AA56-223; A63, 73=AA1-246 (Ala63/73)] and 2.0 µg of a 5×GAL4-Elb-CAT reporter in the absence or presence of the indicated amounts (in µg) of pZIPNeoRas(Leu61). The total amount of expression vector was kept constant and the total amount of transfected DNA was brought to 15 µg using pUC18 and the appropriate amount of pZIPneo. Cells were harvested 28 hours after transfection and CAT activity was determined. Shown are the averages of two experiments, calculated as fold-activation over the level of reporter expression seen in the absence of the GAL4-Jun expressions vectors.

Figure 8B:
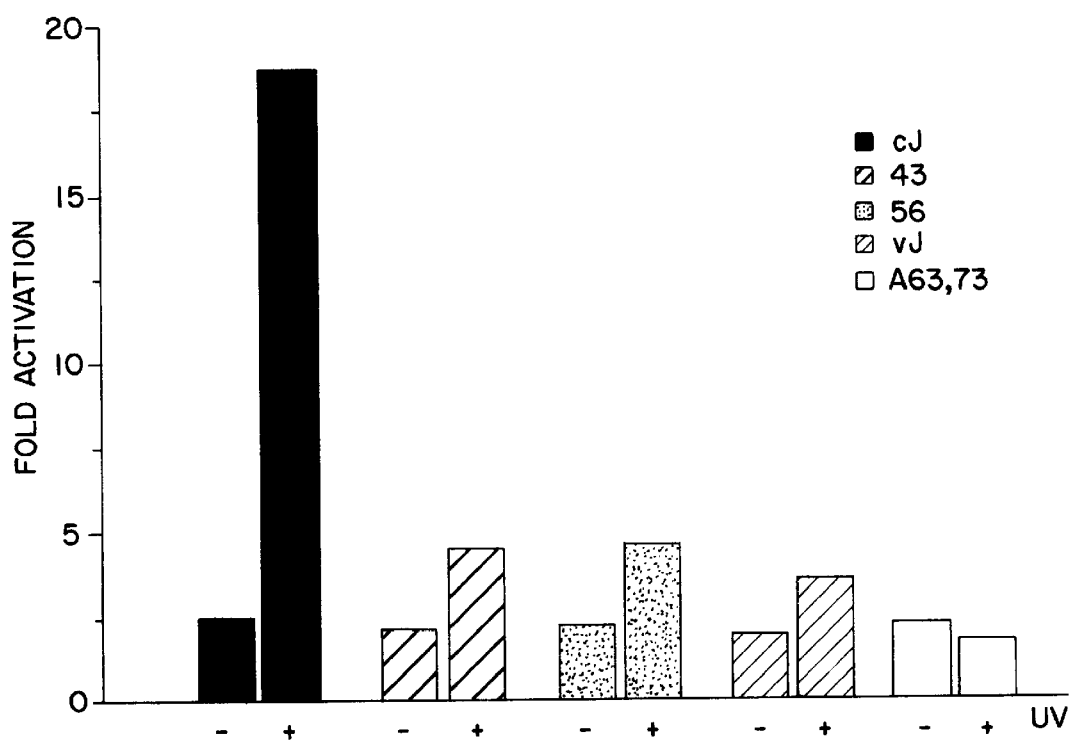

While deletion of AA 1-32 of c-Jun resulted in a small decrease in Ha-Ras responsiveness (9.8-fold induction vs. 19-fold induction for wt GAL4-cJun), deletion of AA 1-42 or 1-55 resulted in a greater decrease in Ha-Ras responsiveness (5.2-fold induction). A similar decrease in Ha-Ras responsiveness was observed upon substitution of c-Jun sequences with v-Jun sequences (4.7-fold induction). In fact, the GAL4-cJun(56-223) and GAL4-vJun chimeras were only 2-fold more responsive than GAL4-cJun(1-246;Ala63/73) in which Ser 63 and 73 were converted to alanines. That chimera exhibited only a marginal response (2-fold) to Ha-Ras. The same set of GAL4-cJun and GAL4-vJun fusion proteins was tested for UV responsiveness. F9 cells were transfected as described above except that instead of cotransfection with pZIPNeoRas, the cells were either exposed or not exposed to 40 J/m2 of UV-C 8 hours after transfection. The cells were harvested and assayed for CAT activity 20 hours later. FIG. 8B shows the averages of two experiments calculated as described above.

As shown in FIG. 8B, those proteins incapable of binding JNK in vitro, were non-responsive to UV in vivo. While the activity of GAL4-cJun(1-223) was stimulated 7.5-fold by UV, the activities of GAL4-cJun(43-223), GAL4-cJun(56-223) and GAL4-vJun were induced only 1.5-fold.

To reveal the role of JNK binding in c-Jun phosphorylation, F9 cells were transfected with c-Jun and v-Jun expression vectors in the absence or presence of an activated Ha-Ras expression vector. UV-irradiation was also used to activate the Ha-Ras pathway (Devary, et al., 1992). v-Jun and c-Jun were isolated by immunoprecipitation from $^{32}$-S or $^{32}$P-labelled F9 cells that were transfected with v-Jun and c-Jun expression vectors in the absence or presence of pZIPNeoRas (Leu6l). The isolated proteins were analyzed by SDS-PAGE and autoradiography. Shown are the results of one typical experiment for each protein. Note that the $^{32}$P-labelled v-Jun autoradiogram was exposed 3 times longer than the corresponding c-Jun autoradiogram to generate signals of similar intensity. v-Jun and c-Jun were isolated from $^{32}$P and $^{32}$S-labelled F9 cells that were transfected with v-Jun or c-Jun expression vectors. One half of the cells were irradiated with UV-C(40 J/m$^2$) for 30 minutes prior to isolation of the Jun proteins by immunoprecipitation. In this case, the c-Jun and v-Jun lanes represent equal autoradiographic exposures. The two arrowheads indicate the migration positions of the two forms of c-Jun (Devary, et al., 1992), whereas the square indicates the migration position of v-Jun.

Figure 9B:
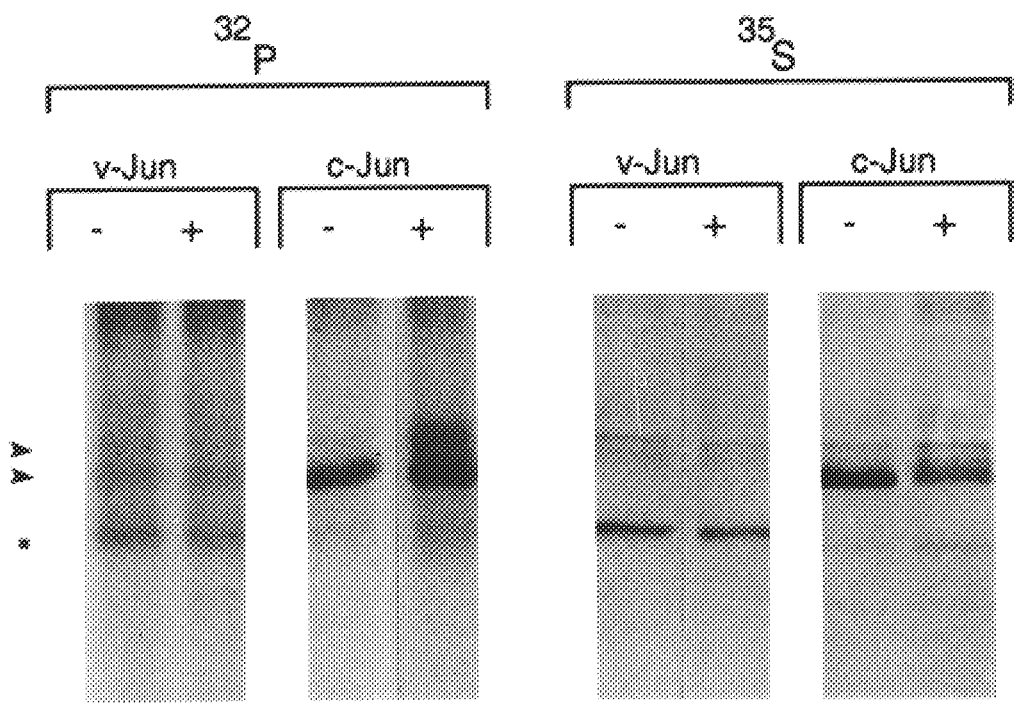

Immunoprecipitation from $^{32}$S-labelled cells showed that c-Jun and v-Jun were expressed at similar levels and that their expression level was not affected by either Ha-Ras (FIG. 9A) or UV (FIG. 9B). Immunoprecipitation from 32P-labeled cells indicated that both Ha-Ras and UV stimulated the phosphorylation of c-Jun, whereas the phosphorylation of v-Jun, whose basal level was several-fold lower than that of c-Jun, was not enhanced by either treatment. As observed previously (Devary, et al., supra, 1991), UV was a stronger inducer of c-Jun phosphorylation resulting in its retarded electrophoretic mobility. Phosphopeptide mapping confirmed that Ha-Ras expression had a much smaller effect on the phosphorylation of v-Jun in comparison to its effect on c-Jun. As shown previously (Smeal, et al., supra, 1991), v-Jun was phosphorylated only on one site which is equivalent to Ser 73 of c-Jun.

EXAMPLE 9

Antisera and proteins c-Jun polyclonal antiserum was described by Binetruy, et al., (*Nature,* 351:122–127, 1991). The anti-CD3 monoclonal antibody OKT3 (Van Wauwe, et al., *J. Immunol.,* 124:2708–2713, 1980) was obtained from Dr. Amnon Altman, La Jolla Institute for Allergy and Immunology, and the anti-CD28 monoclonal antibody 9.3 is described in Hansen, et al., (*Immunogenetics,* 10:247–260, 1980). The anti-ERK2 and anti-ERK antibodies were provided by Drs. M. Weber and M. Cobb (University of Texas Southwestern), respectively. Expression and purification of GST-cJun(1-223) was described (Hibi, et al., *Genes & Dev.,* 7:2135, 1993). The bacterial expression vector for kinase-defective ERK-1 was a gift from Dr. M. Cobb and the recombinant protein was prepared and purified by Dr. J. Hagstrom. MBP was purchased from Sigma.

Cell culture, metabolic labeling, and immunoprecipitation

Jurkat cells were grown in RPMI with 10% fetal calf serum (FCS), 1 mM glutamate, 100 $\mu$/ml penicillin (pen), 100 $\mu$g/ml streptomycin (strep) and 250 ng/ml amphotericin (complete medium). HeLa S3, CV-1 and FR3T3 cells were grown in DMEM supplemented with 10% FCS, 100 $\mu$/ml pen, 100 $\mu$g/ml strep. All cells were cultured at 37° C. with 5% $CO_2$. Mouse thymocytes were prepared from 8 week old Balb/C mice by gradient centrifugation on lymphocyte separation medium (Pharmacia). The lymphocytes were cultured for 5 hours at 37° C. in RPMI+10% FCS, prior to stimulation. Jurkat cells were labelled for 90 minutes with 0.5 mCi/ml $^{32}$P-orthophosphate (ICN Radiochemicals) in medium lacking sodium phosphate. Labelled cells were treated with TPA (Sigma) and A23187 (Calbiochem) 1 $\mu$g/ml as indicated. When used, cyclosporin A (CsA) (Sandoz) 100 ng/ml in ethanol was added 10 minutes prior to cell stimulation. Following stimulation, the labelled cells were washed twice with ice-cold PBS then lysed with RIPA buffer (10 mM Tris pH 7.5, 150 mM NaCl, 2 mM EDTA, 1% Triton-X 100, 1% DOC, 0.1% SDS) supplemented with phosphatase inhibitors (20 mM $\beta$-glycerophosphate, 10 mM p-nitrophenylphosphate, 1 mM $Na_3$ $VO_4$), and protease inhibitors (10 $\mu$g/ml leupeptin, aprotonin, pepstatin and 1 mM phenylmethyl sulfonylfluoride). c-Jun was immunoprecipitated as described (Binetruy, et al., supra., 1992) and analyzed by SDS-PAGE, followed by peptide mapping (Boyle, et al., *Cell,* 64:573–584, 1991; Lin, et al. *Cell,* 70:777–789, 1992). Ha-Ras was immunoprecipitated with Y13-259. Ha-Ras bound nucleotides were extracted and analyzed as described by Satoh, et al., (*Proc. Natl. Acad. Sci., USA,* 15:5993–5997, 1990).

RNA extraction and Northern blot analysis

Exponentially growing Jurkat cells ($10^6$/ml) grown in complete RPMI medium was pretreated with CsA for 15 minutes when applicable, then subjected to various treatments for another 40 minutes. Total cytoplasmic RNA was extracted as previously described (Angel, et al., *Cell,* 49:729–739, 1987). 10 $\mu$g RNA was denatured by incubating with glyoxal for 60 minutes at 55° C. and fractionated on a 1% agarose gel in phosphate buffer. The fractionated RNA was blotted to Zetabind Nylon membrane (CUNO Labs) and hybridized to 32P-labelled cDNA probes specific for c-jun, jun-B, jun-D, c-fos, $\alpha$-tubulin and IL-2.

Protein Kinase assays

Exponentially growing cells were stimulated for the indicated times and hypotonic detergent cellular extracts were prepared as described (Hibi, et al., *Genes and Dev.,* supra, 1993). The solid-state phosphorylation assay for measuring JNK activity was performed by incubated extracts with GSTcJun(1-223)-GSH agarose beads as described (Hibi, et al., supra., 1993) and as in Example 2. ERK1 and 2 activity was assayed by an immunecomplex kinase assay using MBP as a substrate (Minden, et al., *Nature,* 1993).

Reporters, expression vectors and transfections

–79 jun-LUC, –73/+63 Col-LUC, –60/+63 Col-LUC were described previously (Deng and Karin, 1993). The IL2-LUC reporter plasmid was constructed by subcloning the IL-2 promoter (298 bp) from IL2CAT/+1 (Serfling, et al., *EMBO J.,* 8:465–473, 1988) into the p20Luc vector (Deng and Karin, *Genes and Dev.,* 7:479, 1993) between the SacI and KpnI site. The c-Jun expression vector pSRaIIc-Jun was constructed by subcloning the human c-jun HindIII-NotI fragment from pRSVc-Jun (Binetruy, et al., supra., 1991) into pSR$\alpha$II vector by blunt end ligation. pBJ-CNA and pBJ-CNB were from Dr. G. Crabtree, Stanford University. $\beta$-Actin-LUC was from Dr. C. Glass, UCSD.

T Ag Jurkat cells, a derivative of the human Jurkat T-cell line stably transfected with the SV40 large T antigen (a gift from Dr. G. Crabtree) were grown to $10^6$/ml, then resuspended at $2 \times 10^7$/ml in fresh complete medium. $10^7$ cells (0.5 ml) were mixed with reporter plasmids (5 $\mu$g, –79 jun-LUC; 10 $\mu$g, –73/+63 Col-LUC or –60/+63 Col-LUC; 5 $\mu$g IL2-LUC) at room temperature for 10 minutes, then electroporated at 250 V, 960 uF in a 0.4 cm cuvette using a Bio-Rad GenePulser. After electroporation, cells were immediately put on ice for 10 minutes, then resuspended in 10 ml complete medium for 24 hours before stimulation. 0.5 $\mu$g of pSR$\alpha$IIc-Jun were used to transfect $10^7$ Jurkat cells. Luciferase activity was determined as described (Deng and Karin, supra., 1993).

Analysis of GDP and GTP bound to RAS p21

Jurkat cells $10 \times 10^6$ were labelled for 3 hours with $^{32}$P-orthophosphate (ICN Radiochemicals) at 1 mCi/ml in 5 mM of $Na_3VO_4$ phosphate-free DMEM supplemented with 1 mg/ml BSA. Before harvest, cells were stimulated with TPA, 10 ng/ml, A23187, 1 $\mu$g/ml anti-CD3 antibody (OKT3), 10 $\mu$g/ml, anti-CD28 antibody, 2 $\mu$g/ml or their combinations. After treatment for a specified period, cells were washed once immediately with ice cold PBS, twice with ice-cold Tris-Buffered saline (50 mM Tris-HCl, pH 7.5, 20 mM $MgCl_2$, 150 mM NaCl, 10.5% Nonidet P-40/1 $\mu$g/ml of aprotinin, leupeptin, pepstatin and 1 mM phenylmethyl sulfonylfluoride). Ras p21 was immunoprecipitated with monoclonal antibody Y 12-259 (Santa Cruz Biotechnology, Inc., Santa Cruz, Calif.). The GDP/GTP content of Ras was analyzed by TLC as described (Satoh, et al., *Proc. Natl. Acad. Sci., USA,* 15:5993, 1990) and quantitated with an Ambis radioanalytic image system (Ambis, San Diego, Calif.).

EXAMPLE 10

SYNERGISTIC INDUCTION OF AP-1 ACTIVITY DURING T CELL ACTIVATION

During the first stage of T lymphocyte activation, early response genes are rapidly included (Crabtree, *Science,* 243:355,361, 1989; Zipfel, et al., *Mol. Cell Bio.,* 9:1041–1048, 1989). Induction of jun and fos genes during activation of the Jurkat T cell line was investigated. Two different co-stimulatory paradigms were used, one employing TPA and the $Ca^{2+}$ ionophore A23187, and the second based on simultaneous stimulation of the TCR complex with an antibody to its CD3 component (OKT3; Van Wauwe, et al., *J. Immunol.,* 124:2708–2713, 1980) and stimulation of the CD28 auxiliary receptor with an anti-CD28 antibody (9.3; Hansen, et al., *Immunogenetics,* 10:247–260, 1993;

June, et al., *Immunol. Today,* 11:211–216, 1990). Total cytoplasmic RNA was extracted from Jurkat cells that were incubated with 50 ng/ml TPA (T), 1 μg/ml A23187 (A) or 100 ng/ml cyclosporin A (CsA) for 40 minutes, either alone or in combinations, as indicated. After fractionation of 10 μg samples on an agarose gel and transfer to nylon membrane, the level of c-jun, jun-B, jun-D, c-fos and α-tubulin expression was determined by hybridization to random primed cDNA probes.

Second, Jurkat cells were incubated with 10 μg/ml soluble anti-CD3 (OKT3), 2 μg/ml soluble anti-CD28 (9.3) or a combination of 50 ng/ml TPA and 1 μg/ml A23817 (T/A) as indicated for 40 minutes. Total cytoplasmic RNA was isolated and 10 μg samples were analyzed as described above using c-jun, jun-D and c-fos probes. IL-2 induction by the same treatments was measured after 6 hours of stimulation by blot hybridization using IL-2 and a-tubulin specific probes.

Both the first and second costimulatory paradigms induced IL-2 transcription (FIG. 11B). Optimal induction of c-jun also required a combined treatment with TPA and A23187 (FIG. 11A) or anti-CD3 and anti-CD28 (FIG. 11B). The synergistic induction of c-jun by both costimulatory paradigms was partially inhibited by CsA. jun-B was also induced by TPA, but its induction was not affected by A23187 or CsA. Although TPA+A23187 potentiated jun-D expression, this effect was also not inhibited by CsA. As reported by Matilla, et al., (*EMBO J.,* 9:4425–4433, 1990), maximal induction of c-fos also required treatment with TPA+A23187, but was not inhibited by CsA. Therefore sensitivity to CsA is unique to c-jun. While incubation with soluble anti-CD3 led to induction of c-jun and c-fos, only c-jun expression was augmented by simultaneous exposure to anti-CD28.

The effects of the different stimuli on AP-1 transcriptional activity in Jurkat cells were examined using a truncated, AP-1 responsive, human collagenase promoter (Angel, et al., *Cell,* 49:729–739, 1987) fused to the luciferase (LUC) reporter gene. Jurkat cells were transfected with 10 μg of either −73Col-LUC or −60Col-LUC reporter plasmids. 24 hours after transfection, the cells were aliquoted into 24 well plates and incubated for 9 hours with 50 ng/ml TPA, 1 μg/ml A23187 or 100 ng/ml CsA, either alone or in combinations, as indicated. The cells were harvested and luciferase activity was determined. The results shown are averages of three experiments done in triplicates.

While TPA and A23187 administered alone had marginal effects on −73Col-LUC, the two together resulted in its synergistic activation (FIG. 11C). The −60Col-LUC reporter, lacking an AP-1 binding site, was not induced. Induction of −73Col-LUC was inhibited by CsA. Treatment with anti-CD3 and anti-CD28 also resulted in synergistic activation of −73Col-LUC. Similar results were obtained with the AP-1 responsive c-jun promoter. These findings differ from previous measurements of AP-1 activity in Jurkat cells that relied on the use of synthetic promoters containing multiple AP-1 sites (Matilla, et al., supra, 1993; Ullman, et al, *Genes & Dev.,* 7:188–196, 1993). While these findings were reproducible, previous studies indicate that the physiological collagenase and c-jun promoters provide a more accurate and valid measurement of AP-1 transcriptional activity. Indeed, the expression patterns of the collagenase and c-jun reporters are very similar to that of the c-jun gene.

EXAMPLE 11

COSTIMULATION OF c-Jun N-TERMINAL PHOSPHORYLATION IS SUPPRESSED BY CsA

Induction of c-Jun transcription and optimal stimulation of AP-1 correlate with changes in c-Jun phosphorylation (Devary, et al., *Cell,* 71:1081–1091, 1992). The effect of TPA and A23187 on c-Jun phosphorylation in Jurkat cells was examined. To elevate c-Jun expression, Jurkat cells were transfected with a c-Jun expression vector. The cells were labelled with $^{32}$P and c-Jun was immunoprecipitated from cells subjected to various stimuli and analyzed by SDS-PAGE (FIG. 12A). Jurkat cells ($10^6$ cells per lane) were transfected with 0.5 ug of a SRα-cJun expression vector and 24 hours later were labeled for 3 hours with 32P-orthophosphate (1 mCi/ml). After 15 minutes, treatment with 50 ng/ml TPA (T), 1 μg/ml A23187 (A) and 100 ng/ml CsA, either alone or in combination, as indicated, the cells were lysed in RIPA buffer and c-Jun was isolated by immunoprecipitation and analyzed by SDS-PAGE. The c-Jun bands are indicated.

In unstimulated cells, phosphorylated c-Jun migrated as a single band. Treatment with TPA for 15 minutes induced the appearance of slower migrating bands and costimulation with A23187 enhanced this effect, while CsA reduced the $Ca^{++}$ effect. Within the short time frame of this experiment, there were minimal effects on c-Jun expression.

Similar results were obtained by analysis of endogenous c-Jun expression and phosphorylation (FIG. 12B). $2\times10^7$ Jurkat cells were labeled for 3 hours with either $^{35}$S-methionine (900 μCi/ml) or $^{32}$P-orthophosphate (1 mCi/ml). After 15 minutes incubation with 50 ng/ml TPA+1 μg/ml A23178 (T/A) in the absence or presence of and 100 ng/ml CsA or no addition, as indicated, the cells were lysed in RIPA buffer and c-Jun isolated by immunoprecipitation and analyzed by SDS-PAGE. The c-Jun band is indicated. However, due to lower expression levels, some of the slower migrating forms were not clearly visible.

c-Jun phosphorylation was further analyzed by two-dimensional phosphopeptide mapping (FIG. 12C). This analysis included all the isoforms of c-Jun. All of the c-Jun specific protein bands shown in FIG. 12A, isolated from equal numbers of cells, were excised from the gel and subjected to tryptic phosphopeptide mapping. Shown is a typical result (this experiment was repeated at least three times). N-nonstimulated cells; T-cells treated with 50 ng/ml TPA; T/A: cells treated with 50 ng/ml TPA and 1 μg/ml A23187; T/A+CsA: cells treated with T/A and 100 ng/ml CsA. a,b,c,x and y correspond to the various tryptic phosphopeptides of c-Jun, previously described by Boyle, et al., (*Cell,* 64:573–584, 1991) and Smeal, et al., (*Nature,* 354:494–496, 1991). T1 and T2 correspond to the minor phosphorylation sites; Thr91, 93 and 95 (Hibi, et al., *Genes & Dev.,* 7:000, 1993).

While the intensity of spot b, a doubly phosphorylated tryptic peptide containing the C-terminal phosphorylation sites of c-Jun (Boyle, et al., *Cell,* 64:573–584, 1991; Lin, et al., *Cell,* 70:777–789, 1992), was more or less invariant, TPA treatment resulted in a small increase in the intensity of the monophosphorylated form of this peptide (spot c) at the expense of the triple phosphorylated form (spot a). This effect was also observed in response to costimulation with TPA+A23187. In contrast to HeLa cells and fibroblasts (Boyle, et al., supra, 1991; Minden, et al., *Nature,* 1993), TPA treatment of Jurkat cells resulted in increased phosphorylation of the N-terminal sites, corresponding to Ser63 (spot y) and Ser73 (spot x) and this effect was strongly enhanced by A23187. CsA prevented the enhancement of N-terminal phosphorylation by A23187.

EXAMPLE 12

SYNERGISTIC ACTIVATION OF JNK

Studies were done to determine whether enhanced N-terminal c-Jun phosphorylation in response to TPA+

A23187 was due to synergistic activation of JNK, the protein kinase that binds to c-Jun and phosphorylates its N-terminal sites. JNK exists in two forms, 46 kD and 55 kD in size, both of which are activated by external stimuli (Hibi, et al., supra, 1993; Deng, et al., supra, 1993). In-gel kinase assays indicated that both forms of JNK were activated by TPA (FIG. 13A). Whole cell extracts (WCE) of Jurkat cells incubated with TPA (T, 50 ng/ml), A23187 (A, 1 µg/ml) or CsA (100 ng/ml) for 15 minutes, alone or in combination, were separated by SDS-PAGE (100 µg protein/lane) on gels that were cast in the absence or presence of GST-cJun (1-223). The gels were subjected to renaturation protocol and incubated in kinase buffer containing $\gamma$-$^{32}$P-ATP. The protein bands corresponding to the 55 kD and 46 kD forms of JNK are indicated.

While A23187 treatment by itself did not activate JNK, it potentiated its activation by TPA. CsA blocked this costimulatory effect.

JNK can be retained on GSTcJun-glutathione (GSH) agarose affinity resin and its kinase activity measured by phosphorylation of GSTcJun. WCE (50 µg) of Jurkat cells treated as described above were incubated with 5 µl of GSH agarose beads coated with 10 µg GST-cJun (1-223) for 12 hours at 4° C. After extensive washing, the beads were incubated in kinase buffer containing $\gamma$-$^{32}$P-ATP for 20 minutes at 30° C., after which the proteins were dissociated by incubation in SDS sample buffer and separated by SDS-PAGE (FIG. 13B). The 49 kD band corresponds to GST-cJun (1-223). The faster migrating bands are degradation products (Hibi, et al., supra, 1993).

This solid-state assay also indicated that TPA treatment resulted in activation of JNK, which was strongly potentiated by A23187, which by itself had no effect. This synergistic activation of JNK was inhibited by CsA (FIG. 13B). To prove that the solid-state assay measures the activity of the same polypeptides identified by the in-gel kinase assay, JNK was first isolated on GSTcJun-GSH agarose beads and then analyzed it by an in-gel kinase assay. Both the 55 and 46 kD forms of JNK bound to GSTcJun and were regulated in the same manner revealed by the binding assay (FIG. 13C). WCE (200 µg) of Jurkat cells treated as described in FIG. 13A were incubated with GST-cJun(1-223)-GSH agarose beads as described above and the bound fraction was eluted in SDS sample buffer and separated by SDS-PAGE on a gel containing GST-cJun(1-223). The gel was renatured and incubated in kinase buffer containing $\gamma$-$^{32}$P-ATP to label the JNK polypeptides.

EXAMPLE 13

COSTIMULATION BY Ca$^{++}$ IS UNIQUE TO JNK AND T LYMPHOCYTES

We examined whether elevated intracellular Ca$^{++}$ affects JNK activation in other cells. JNK activity was weakly stimulated by TPA in CV1 and FR3T3 cells, but not in PC12 cells (FIG. 14). Cultures of FR3T3, CV-1, PC12 and mouse thymocytes were incubated for 15 minutes in the presence of TPA (50 ng/ml, T), A23817 (1 µg/ml, A) and/or CsA (100 ng/ml), as indicated. WCE prepared from 2–4×10$^5$ cells for the established cell lines and 1.5×10$^6$ cells for primary thymocytes were incubated with GSTcJun(1-223)-GSH agarose beads. After washing, JNK activity was determined by solid-state phosphorylation assay as described above.

In none of these cells was JNK activity affected by A23187 or CsA treatment. Similar results were obtained in HeLa, HepG2 and Gc cells. By contrast, the regulation of JNK activity in mouse thymocytes was similar to that observed in Jurkat cells. TPA induced a moderate increase in JNK activity which was enhanced by A23187 and that costimulation was inhibited by CsA (FIG. 14).

JNK is a proline-directed protein kinase activated by extracellular stimuli (Hibi, et al., supra, 1993). In that respect, it resembles the ERK1 and 2 MAP kinases (Boulton, et al., Cell, 65:663–675, 1991). Since ERK1 and 2 appear to be involved in induction of c-fos (Gille, et al., Nature, 358:414–417, 1992; Marais, et al., Cell, 73:381–393, 1993) and could thereby participate in T cell activation, their regulation was examined. ERK1 and ERK2 activities were measured in both Jurkat and mouse thymocytes using an immunecomplex kinase assay and myelin basic protein (MBP) as a substrate. Recombinant, kinase-defective ERK1 was also used a substrate for assaying MEK, the protein kinase responsible for activation of ERK1 and 2 (Crews, et al., Science, 258:478–480, 1992). Both ERK and MEK activities were fully stimulated by TPA treatment of either Jurkat cells or mouse thymocytes (FIG. 15).

WCE (5 µg) of Jurkat (FIG. 15, panel A) or mouse thymocytes (panel C) were incubated with 1 µg of kinase-defective ERK1 in kinase buffer containing $\gamma$-$^{32}$P-ATP for 20 minutes. The phosphorylated proteins were separated by SDS-PAGE and the band corresponding to the mutant ERK1 is indicated. WCE (20 µg) of Jurkat (panel B) or mouse thymocytes (panel C) that were treated as described above were immunoprecipitated with anti-ERK antibodies (a gift from Dr. M. Weber). The immune complexes were washed and incubated in kinase buffer containing $\gamma$-$^{32}$P-ATP and 2 µg MBP for 15 minutes at 30° C. The phosphorylated proteins were separated by SDS-PAGE. The band corresponding to phosphorylated MBP is indicated. A23187 and CsA had no effect on either activity.

EXAMPLE 14

SYNERGISTIC ACTIVATION OF JNK BY ANTI-CD3 AND ANTI-CD28

If JNK plays a central role in signal integration during T cell activation, then other costimulatory paradigms should also cause its synergistic activation. The regulation of JNK in response to T cell activation with anti-CD3 and anti-CD28 antibodies was examined. Jurkat cells (1×10$^7$) were incubated for 15 minutes with either normal mouse serum, 1 µg/ml anti-CD3 and/or 2 µg/ml anti-CD28, in the absence or presence of 100 ng/ml CsA, as indicated. WCE were prepared and 100 µg samples were analyzed for JNK activation using the ingel kinase assay, as described above.

While incubation of Jurkat cells with either soluble anti-CD3 or soluble anti-CD28 alone had a negligible effect on JNK activity, simultaneous incubation with both antibodies resulted in strong synergistic activation of both forms (FIG. 16A).

WCE (50 µg) of Jurkat cells treated as described above were incubated with GSTcJun(1-223)-GSH agarose beads and assayed for JNK activity using the solid-state kinase assay. The same WCE (20 µg) were immunoprecipitated with anti-ERK2 antibodies and assayed for MBP-kinase activity. CsA partially attenuated this effect. By contrast, incubation with soluble anti-CD3 was sufficient for efficient activation of ERK2, which was not enhanced by costimulation with anti-CD28, nor was it inhibited by CsA (FIG. 16B).

To further investigate the nature of signal integration by JNK, the effect of a suboptimal dose of TPA was examined, which by itself does not lead to JNK activation on the responses to either anti-CD3 or anti-CD28 (FIG. 16C). WCE (50 μg) of Jurkat cells treated as described in Panel A with various stimuli alone or their combinations were incubated with GSTcJun(1-223)-GSH agarose beads and assayed for JNK activity using solid-state kinase assay. The same samples (20 μg) were also assayed for MBP-kinase activity as described in FIG. 16B.

Together with A23187, this suboptimal dose of TPA resulted in a strong synergistic activation of JNK but not ERK2. The activation of JNK was completely inhibited by CsA. The suboptimal dose of TPA also led to strong synergistic activation of JNK together with either anti-CD3 or anti-CD28. ERK2, on the other hand, was fully activated by anti-CD3 and suboptimal TPA, which by itself led to partial activation of ERK2, had no further effect. Exposure to anti-CD28 did not augment the activation of ERK2 by TPA. JNK was also efficiently activated by combined treatment with anti-CD3+A23187, but not by anti-CD28+A23187.

EXAMPLE 15

ACTIVATION OF Ha-Ras

The effects of the various treatments on Ha-Ras activation were examined and the results shown in FIG. 17. Jurkat cells ($2\times10^6$ cells per point) labeled with 0.4 mCi of $^{32}$P-orthophosphate for 3 hours were incubated with nonspecific antibody (1 μg/ml mouse IgG; control), 1 μg/ml anti-CD3, 2 μg/ml anti-CD28, 10 ng/ml TPA or 500 ng/ml A23187 (A), as indicated. After 2 minutes, the cells were harvested, lysed and Ha-Ras was isolated by immunoprecipitation. The guanine nucleotide bound to Ha-Ras were extracted, separated by thin layer chromatography and quantitiated as described in EXAMPLE 9. The values shown represent the averages of two separate experiments done in duplicates. Jurkat cells were labeled with $^{32}$P-orthophosphate and stimulated with either TPA or anti-CD3 as described above. At the indicated time points, the cells were harvested and the GTP content of Ha-Ras was determined as described directly above.

Whereas an optimal dose of TPA and exposure to soluble anti-CD3 led to activation of Ha-Ras, measured by an increase in its GTP content, soluble anti-CD28 had no effect on Ha-Ras activity (FIG. 17A). The activation of Ha-Ras by either anti-CD3 or TPA was not augmented by costimulation with either anti-CD28 or A23187, respectively. While the activation of Ha-Ras by TPA persisted for at least 20 minutes, the response to soluble anti-CD3 was highly transient (FIG. 17B). Therefore, signal integration must occur downstream of Ha-Ras.

The foregoing is meant to illustrate, but not to limit, the scope of the invention. Indeed, those of ordinary skill in the art can readily envision and produce further embodiments, based on the teachings herein, without undue experimentation.

SEQUENCE ID LISTING

SEQ ID NO: 1 is the amino acid sequence of residues 33–79 of c-Jun.
SEQ ID NO: 2 is the nucleotide sequence for an N-terminal primer used for producing c-Jun truncation mutants.
SEQ ID NO: 3 is the nucleotide sequence for an N-terminal primer used for producing c-Jun truncation mutants.
SEQ ID NO: 4 is the nucleotide sequence for an N-terminal primer used for producing c-Jun truncation mutants.
SEQ ID NO: 5 is the nucleotide sequence for an N-terminal primer used for producing c-Jun truncation mutants.
SEQ ID NO: 6 is the nucleotide sequence for an N-terminal primer used for producing c-Jun truncation mutants.
SEQ ID NO: 7 is the nucleotide sequence for a C-terminal primer used for producing c-Jun truncation mutants.
SEQ ID NO: 8 is the nucleotide sequence for a C-terminal primer used for producing c-Jun truncation mutants.
SEQ ID NO: 9 is the nucleotide sequence and deduced amino acid sequence for c-jun and c-Jun.
SEQ ID NO: 10 is the deduced amino acid sequence of c-Jun.

---

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 47 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: c-Jun/JNK binding site ( i x ) FEATURE:
        ( A ) NAME/KEY: Peptide
        ( B ) LOCATION: 1..47

( x i ) SEQUENCE DESCRIPTION: SEQ ID NO:1:

```
Ile  Leu  Lys  Gln  Ser  Met  Thr  Leu  Asn  Leu  Ala  Asp  Pro  Val  Gly  Ser
 1              5                        10                           15
```

```
        Leu   Lys   Pro   His   Leu   Arg   Ala   Lys   Asn   Ser   Asp   Leu   Leu   Thr   Ser   Pro
                          20                        25                        30

Asp   Val   Gly   Leu   Leu   Lys   Leu   Ala   Ser   Pro   Glu   Leu   Glu   Arg   Leu
                          35                        40                        45
```

( 2 ) INFORMATION FOR SEQ ID NO:2:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: N-terminal primer ( i x ) FEATURE:
        ( A ) NAME/KEY: CDS
        ( B ) LOCATION: 1..35

( x i ) SEQUENCE DESCRIPTION: SEQ ID NO:2:

```
TCTGCAGGAT   CCCCATGACT   GCAAAGATGG   AAACG                                    35
```

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: N-terminal primer ( i x ) FEATURE:
        ( A ) NAME/KEY: CDS
        ( B ) LOCATION: 1..34

( x i ) SEQUENCE DESCRIPTION: SEQ ID NO:3:

```
TCTGCAGGAT   CCCCGACGAT   GCCCTCAACG   CCTC                                     34
```

( 2 ) INFORMATION FOR SEQ ID NO:4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: N-terminal primer ( i x ) FEATURE:
        ( A ) NAME/KEY: CDS
        ( B ) LOCATION: 1..35

( x i ) SEQUENCE DESCRIPTION: SEQ ID NO:4:

```
TCTGCAGGAT   CCCCGAGAGC   GGACCTTATG   GCTAC                                    35
```

( 2 ) INFORMATION FOR SEQ ID NO:5:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
    ( B ) CLONE: N-terminal primer ( i x ) FEATURE:
    ( A ) NAME/KEY: CDS
    ( B ) LOCATION: 1..35

( x i ) SEQUENCE DESCRIPTION: SEQ ID NO:5:

TCTGCAGGAT CCCCGCCGAC CCAGTGGGGA GCCTG  35

( 2 ) INFORMATION FOR SEQ ID NO:6:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: N-terminal primer ( i x ) FEATURE:
        ( A ) NAME/KEY: CDS
        ( B ) LOCATION: 1..35

( x i ) SEQUENCE DESCRIPTION: SEQ ID NO:6:

TCTGCAGGAT CCCCAAGAAC TCGGACCTCC TCACC  35

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: C-terminal primer ( i x ) FEATURE:
        ( A ) NAME/KEY: CDS
        ( B ) LOCATION: 1..30

( x i ) SEQUENCE DESCRIPTION: SEQ ID NO:7:

TGAATTCTGC AGGCGCTCCA GCTCGGGCGA  30

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: C-terminal primer ( i x ) FEATURE:
        ( A ) NAME/KEY: CDS
        ( B ) LOCATION: 1..33

( x i ) SEQUENCE DESCRIPTION: SEQ ID NO:8:

TGAATTCCTG CAGGTCGGCG TGGTGGTGAT GTG  33

( 2 ) INFORMATION FOR SEQ ID NO:9:

( i ) SEQUENCE CHARACTERISTICS:
        ( A ) LENGTH: 2099 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Jun ( i x ) FEATURE:
        ( A ) NAME/KEY: CDS
        ( B ) LOCATION: 414..1406

( x i ) SEQUENCE DESCRIPTION: SEQ ID NO:9:

```
GAATTCCGGG  GCGGCCAAGA  CCCGCCGCCG  GCCGGCCACT  GCAGGGTCCG  CACTGATCCG        60

CTCCGGCGGA  GAGCCGCTGC  TCTGGGAAGT  GAGTTCGCCT  GCGGACTCCG  AGGAACCGCT       120

GCGCACGAAG  AGCGCTCAGT  GAGTGACCGC  GACTTTTCAA  AGCCGGGTAG  CGCGCGCGAG       180

TCGACAAGTA  AGAGTGCGGG  AGGCATCTTA  ATTAACCCTG  CGCTCCCTGG  AGCGAGCTGG       240

TGAGGAGGGC  GCAGCGGGGA  CGACAGCCAG  CGGGTGCGTG  CGCTCTTAGA  GAAACTTTCC       300

CTGTCAAAGG  CTCCGGGGGG  CGCGGGTGTC  CCCCGCTTGC  CAGAGCCCTG  TTGCGGCCCC       360

GAAACTTGTG  CGCGCACGCC  AAACTAACCT  CACGTGAAGT  GACGGACTGT  TCT ATG          416
                                                              Met
                                                              1

ACT  GCA  AAG  ATG  GAA  ACG  ACC  TTC  TAT  GAC  GAT  GCC  CTC  AAC  GCC  TCG   464
Thr  Ala  Lys  Met  Glu  Thr  Thr  Phe  Tyr  Asp  Asp  Ala  Leu  Asn  Ala  Ser
               5                        10                      15

TTC  CTC  CCG  TCC  GAG  AGC  GGA  CCT  TAT  GGC  TAC  AGT  AAC  CCC  AAG  ATC   512
Phe  Leu  Pro  Ser  Glu  Ser  Gly  Pro  Tyr  Gly  Tyr  Ser  Asn  Pro  Lys  Ile
              20                        25                      30

CTG  AAA  CAG  AGC  ATG  ACC  CTG  AAC  CTG  GCC  GAC  CCA  GTG  GGG  AGC  CTG   560
Leu  Lys  Gln  Ser  Met  Thr  Leu  Asn  Leu  Ala  Asp  Pro  Val  Gly  Ser  Leu
         35                       40                       45

AAG  CCG  CAC  CTC  CGC  GCC  AAG  AAC  TCG  GAC  CTC  CTC  ACC  TCG  CCC  GAC   608
Lys  Pro  His  Leu  Arg  Ala  Lys  Asn  Ser  Asp  Leu  Leu  Thr  Ser  Pro  Asp
50                       55                       60                       65

GTG  GGG  CTG  CTC  AAG  CTG  GCG  TCG  CCC  GAG  CTG  GAG  CGC  CTG  ATA  ATC   656
Val  Gly  Leu  Leu  Lys  Leu  Ala  Ser  Pro  Glu  Leu  Glu  Arg  Leu  Ile  Ile
                   70                       75                       80

CAG  TCC  AGC  AAC  GGG  CAC  ATC  ACC  ACC  ACG  CCG  ACC  CCC  ACC  CAG  TTC   704
Gln  Ser  Ser  Asn  Gly  His  Ile  Thr  Thr  Thr  Pro  Thr  Pro  Thr  Gln  Phe
                   85                       90                       95

CTG  TGC  CCC  AAG  AAC  GTG  ACA  GAT  GAG  CAG  GAG  GGG  TTC  GCC  GAG  GGC   752
Leu  Cys  Pro  Lys  Asn  Val  Thr  Asp  Glu  Gln  Glu  Gly  Phe  Ala  Glu  Gly
              100                      105                      110

TTC  GTG  CGC  GCC  CTG  GCC  GAA  CTG  CAC  AGC  CAG  AAC  ACG  CTG  CCC  AGC   800
Phe  Val  Arg  Ala  Leu  Ala  Glu  Leu  His  Ser  Gln  Asn  Thr  Leu  Pro  Ser
         115                      120                      125

GTC  ACG  TCG  GCG  GCG  CAG  CCG  GTC  AAC  GGG  GCA  GGC  ATG  GTG  GCT  CCC   848
Val  Thr  Ser  Ala  Ala  Gln  Pro  Val  Asn  Gly  Ala  Gly  Met  Val  Ala  Pro
130                      135                      140                      145

GCG  GTA  GCC  TCG  GTG  GCA  GGG  GGC  AGC  GGC  AGC  GGC  GGC  TTC  AGC  GCC   896
Ala  Val  Ala  Ser  Val  Ala  Gly  Gly  Ser  Gly  Ser  Gly  Gly  Phe  Ser  Ala
                   150                      155                      160

AGC  CTG  CAC  AGC  GAG  CCG  CCG  GTC  TAC  GCA  AAC  CTC  AGC  AAC  TTC  AAC   944
Ser  Leu  His  Ser  Glu  Pro  Pro  Val  Tyr  Ala  Asn  Leu  Ser  Asn  Phe  Asn
              165                      170                      175
```

| | | | | | | | | | | | | | | | | |
|---|---|---|---|---|---|---|---|---|---|---|---|---|---|---|---|---|
| CCA | GGC | GCG | CTG | AGC | AGC | GGC | GGC | GGG | GCG | CCC | TCC | TAC | GGC | GCG | GCC | 992 |
| Pro | Gly | Ala | Leu | Ser | Ser | Gly | Gly | Gly | Ala | Pro | Ser | Tyr | Gly | Ala | Ala | |
| | | 180 | | | | | 185 | | | | | 190 | | | | |
| GGC | CTG | GCC | TTT | CCC | GCG | CAA | CCC | CAG | CAG | CAG | CAG | CAG | CCG | CCG | CAC | 1040 |
| Gly | Leu | Ala | Phe | Pro | Ala | Gln | Pro | Gln | Gln | Gln | Gln | Gln | Pro | Pro | His | |
| | 195 | | | | | 200 | | | | | 205 | | | | | |
| CAC | CTG | CCC | CAG | CAG | ATG | CCC | GTG | CAG | CAC | CCG | CGG | CTG | CAG | GCC | CTG | 1088 |
| His | Leu | Pro | Gln | Gln | Met | Pro | Val | Gln | His | Pro | Arg | Leu | Gln | Ala | Leu | |
| 210 | | | | | 215 | | | | | 220 | | | | | 225 | |
| AAG | GAG | GAG | CCT | CAG | ACA | GTG | CCC | GAG | ATG | CCC | GGC | GAG | ACA | CCG | CCC | 1136 |
| Lys | Glu | Glu | Pro | Gln | Thr | Val | Pro | Glu | Met | Pro | Gly | Glu | Thr | Pro | Pro | |
| | | | | 230 | | | | | 235 | | | | | 240 | | |
| CTG | TCC | CCC | ATC | GAC | ATG | GAG | TCC | CAG | GAG | CGG | ATC | AAG | GCG | GAG | AGG | 1184 |
| Leu | Ser | Pro | Ile | Asp | Met | Glu | Ser | Gln | Glu | Arg | Ile | Lys | Ala | Glu | Arg | |
| | | | 245 | | | | | 250 | | | | | 255 | | | |
| AAG | CGC | ATG | AGG | AAC | CGC | ATC | GCT | GCC | TCC | AAG | TGC | CGA | AAA | AGG | AAG | 1232 |
| Lys | Arg | Met | Arg | Asn | Arg | Ile | Ala | Ala | Ser | Lys | Cys | Arg | Lys | Arg | Lys | |
| | | 260 | | | | | 265 | | | | | 270 | | | | |
| CTG | GAG | AGA | ATC | GCC | CGG | CTG | GAG | GAA | AAA | GTG | AAA | ACC | TTG | AAA | GCT | 1280 |
| Leu | Glu | Arg | Ile | Ala | Arg | Leu | Glu | Glu | Lys | Val | Lys | Thr | Leu | Lys | Ala | |
| | 275 | | | | | 280 | | | | | 285 | | | | | |
| CAG | AAC | TCG | GAG | CTG | GCG | TCC | ACG | GCC | AAC | ATG | CTC | AGG | GAA | CAG | GTG | 1328 |
| Gln | Asn | Ser | Glu | Leu | Ala | Ser | Thr | Ala | Asn | Met | Leu | Arg | Glu | Gln | Val | |
| 290 | | | | | 295 | | | | | 300 | | | | | 305 | |
| GCA | CAG | CTT | AAA | CAG | AAA | GTC | ATG | AAC | CAC | GTT | AAC | AGT | GGG | TGC | CAA | 1376 |
| Ala | Gln | Leu | Lys | Gln | Lys | Val | Met | Asn | His | Val | Asn | Ser | Gly | Cys | Gln | |
| | | | | 310 | | | | | 315 | | | | | 320 | | |
| CTC | ATG | CTA | ACG | CAG | CAG | TTG | CAA | ACA | TTT | TGAAGAGAGA | CCGTCGGGGG | | | | | 1426 |
| Leu | Met | Leu | Thr | Gln | Gln | Leu | Gln | Thr | Phe | | | | | | | |
| | | | 325 | | | | | 330 | | | | | | | | |

| | | | | | |
|---|---|---|---|---|---|
| CTGAGGGGCA | ACGAAGAAAA | AAAATAACAC | AGAGAGACAG | ACTTGAGAAC | TTGACAAGTT | 1486 |
| GCGACGGAGA | GAAAAAAGAA | GTGTCCGAGA | ACTAAAGCCA | AGGGTATCCA | AGTTGGACTG | 1546 |
| GGTTCGGTCT | GACGGCGCCC | CCAGTGTGCA | CGAGTGGGAA | GGACTTGGTC | GCGCCCTCCC | 1606 |
| TTGGCGTGGA | GCCAGGGAGC | GGCCGCCTGC | GGGCTGCCCC | GCTTTGCGGA | CGGGCTGTCC | 1666 |
| CCGCGCGAAC | GGAACGTTGG | ACTTTCGTTA | ACATTGACCA | AGAACTGCAT | GGACCTAACA | 1726 |
| TTCGATCTCA | TTCAGTATTA | AAGGGGGGAG | GGGGAGGGGG | TTACAAACTG | CAATAGAGAC | 1786 |
| TGTAGATTGC | TTCTGTAGTA | CTCCTTAAGA | ACACAAAGCG | GGGGGAGGGT | TGGGGAGGGG | 1846 |
| CGGCAGGAGG | GAGGTTTGTG | AGAGCGAGGC | TGAGCCTACA | GATGAACTCT | TTCTGGCCTG | 1906 |
| CTTTCGTTAA | CTGTGTATGT | ACATATATAT | ATTTTTAAT | TTGATTAAAG | CTGATTACTG | 1966 |
| TCAATAAACA | GCTTCATGCC | TTTGTAAGTT | ATTTCTTGTT | TGTTTGTTTG | GGTATCCTGC | 2026 |
| CCAGTGTTGT | TTGTAAATAA | GAGATTTGGA | GCACTCTGAG | TTTACCATTT | GTAATAAAGT | 2086 |
| ATATAATTTT | TTT | | | | | 2099 |

( 2 ) INFORMATION FOR SEQ ID NO:10:

( i ) SEQUENCE CHARACTERISTICS:
        ( A ) LENGTH: 331 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | | |
|---|---|---|---|---|---|---|---|---|---|---|---|---|---|---|---|
| Met | Thr | Ala | Lys | Met | Glu | Thr | Thr | Phe | Tyr | Asp | Asp | Ala | Leu | Asn | Ala |
| 1 | | | | 5 | | | | | 10 | | | | | 15 | |
| Ser | Phe | Leu | Pro | Ser | Glu | Ser | Gly | Pro | Tyr | Gly | Tyr | Ser | Asn | Pro | Lys |

|   |   |   |   |   | 20 |   |   |   |   | 25 |   |   |   |   | 30 |   |   |
|---|---|---|---|---|---|---|---|---|---|---|---|---|---|---|---|---|---|
| Ile | Leu | Lys<br>35 | Gln | Ser | Met | Thr | Leu | Asn<br>40 | Leu | Ala | Asp | Pro<br>45 | Val | Gly | Ser |
| Leu | Lys<br>50 | Pro | His | Leu | Arg | Ala<br>55 | Lys | Asn | Ser | Asp | Leu<br>60 | Leu | Thr | Ser | Pro |
| Asp<br>65 | Val | Gly | Leu | Leu | Lys<br>70 | Leu | Ala | Ser | Pro | Glu<br>75 | Leu | Glu | Arg | Leu | Ile<br>80 |
| Ile | Gln | Ser | Ser | Asn<br>85 | Gly | His | Ile | Thr | Thr<br>90 | Thr | Pro | Thr | Pro | Thr<br>95 | Gln |
| Phe | Leu | Cys | Pro<br>100 | Lys | Asn | Val | Thr | Asp<br>105 | Glu | Gln | Glu | Gly | Phe<br>110 | Ala | Glu |
| Gly | Phe | Val<br>115 | Arg | Ala | Leu | Ala | Glu<br>120 | Leu | His | Ser | Gln | Asn<br>125 | Thr | Leu | Pro |
| Ser | Val<br>130 | Thr | Ser | Ala | Ala | Gln<br>135 | Pro | Val | Asn | Gly | Ala<br>140 | Gly | Met | Val | Ala |
| Pro<br>145 | Ala | Val | Ala | Ser | Val<br>150 | Ala | Gly | Gly | Ser | Gly<br>155 | Ser | Gly | Gly | Phe | Ser<br>160 |
| Ala | Ser | Leu | His | Ser<br>165 | Glu | Pro | Pro | Val | Tyr<br>170 | Ala | Asn | Leu | Ser | Asn<br>175 | Phe |
| Asn | Pro | Gly | Ala<br>180 | Leu | Ser | Ser | Gly | Gly<br>185 | Gly | Ala | Pro | Ser | Tyr<br>190 | Gly | Ala |
| Ala | Gly | Leu<br>195 | Ala | Phe | Pro | Ala | Gln<br>200 | Pro | Gln | Gln | Gln | Gln<br>205 | Gln | Pro | Pro |
| His | His<br>210 | Leu | Pro | Gln | Gln | Met<br>215 | Pro | Val | Gln | His | Pro<br>220 | Arg | Leu | Gln | Ala |
| Leu<br>225 | Lys | Glu | Glu | Pro | Gln<br>230 | Thr | Val | Pro | Glu | Met<br>235 | Pro | Gly | Glu | Thr | Pro<br>240 |
| Pro | Leu | Ser | Pro | Ile<br>245 | Asp | Met | Glu | Ser | Gln<br>250 | Glu | Arg | Ile | Lys | Ala<br>255 | Glu |
| Arg | Lys | Arg | Met<br>260 | Arg | Asn | Arg | Ile | Ala<br>265 | Ala | Ser | Lys | Cys | Arg<br>270 | Lys | Arg |
| Lys | Leu | Glu<br>275 | Arg | Ile | Ala | Arg | Leu<br>280 | Glu | Glu | Lys | Val | Lys<br>285 | Thr | Leu | Lys |
| Ala | Gln<br>290 | Asn | Ser | Glu | Leu | Ala<br>295 | Ser | Thr | Ala | Asn | Met<br>300 | Leu | Arg | Glu | Gln |
| Val<br>305 | Ala | Gln | Leu | Lys | Gln<br>310 | Lys | Val | Met | Asn | His<br>315 | Val | Asn | Ser | Gly | Cys<br>320 |
| Gln | Leu | Met | Leu | Thr<br>325 | Gln | Gln | Leu | Gln | Thr<br>330 | Phe |   |   |   |   |   |

We claim:

1. A method of treating a cell proliferative disorder associated with c-Jun N-terminal kinase having a molecular weight of 46 kD or 55 kD as determined by reducing SDS-PAGE; having serine and threonine kinase activity; and phosphorylating the c-Jun N-terminal activation domain, comprising administering to a subject with the disorder, a therapeutically effective amount of reagent which modulates the kinase activity.

2. The method of claim 1, wherein the reagent is an antisense polynucleotide sequence.

3. The method of claim 1, wherein the reagent is an antibody.

* * * * *